(12) United States Patent
Griesgraber et al.

(10) Patent No.: US 11,370,788 B2
(45) Date of Patent: Jun. 28, 2022

(54) SUBSTITUTED IMIDAZO[4,5-C]QUINOLINE COMPOUNDS WITH AN N-1 BRANCHED GROUP

(71) Applicant: 3M INNOVATIVE PROPERTIES COMPANY, St. Paul, MN (US)

(72) Inventors: George W. Griesgraber, Eagan, MN (US); Kevin J. Bechtold, St. Paul, MN (US)

(73) Assignee: 3M Innovative Properties Company, St. Paul, MN (US)

(*) Notice: Subject to any disclaimer, the term of this patent is extended or adjusted under 35 U.S.C. 154(b) by 187 days.

(21) Appl. No.: 15/733,519

(22) PCT Filed: Feb. 25, 2019

(86) PCT No.: PCT/IB2019/051510
§ 371 (c)(1),
(2) Date: Aug. 19, 2020

(87) PCT Pub. No.: WO2019/166937
PCT Pub. Date: Sep. 6, 2019

(65) Prior Publication Data
US 2020/0385379 A1 Dec. 10, 2020

Related U.S. Application Data

(60) Provisional application No. 62/636,367, filed on Feb. 28, 2018.

(51) Int. Cl.
*C07D 471/04* (2006.01)
(52) U.S. Cl.
CPC .................. *C07D 471/04* (2013.01)
(58) Field of Classification Search
CPC .................................................. C07D 471/04
USPC ....................................................... 514/293
See application file for complete search history.

(56) References Cited

U.S. PATENT DOCUMENTS

| | | |
|---|---|---|
| 3,700,674 A | 10/1972 | Diehl |
| 4,689,338 A | 8/1987 | Gerster |
| 5,352,784 A | 10/1994 | Nikolaides |
| 5,389,640 A | 2/1995 | Gerster |
| 5,446,153 A | 8/1995 | Lindstrom |
| 6,039,969 A | 3/2000 | Tomai |
| 6,110,929 A | 8/2000 | Gerster |
| 6,194,425 B1 | 2/2001 | Gerster |
| 6,200,592 B1 | 3/2001 | Tomai |
| 6,331,539 B1 | 12/2001 | Crooks |
| 6,451,810 B1 | 9/2002 | Coleman |
| 6,664,264 B2 | 12/2003 | Dellaria |
| 7,288,550 B2 * | 10/2007 | Dellaria .................. A61P 31/02 546/82 |
| 7,544,697 B2 | 6/2009 | Hays |
| 7,884,207 B2 | 2/2011 | Stoermer |
| 7,915,281 B2 | 3/2011 | Moser |
| 7,923,560 B2 | 4/2011 | Wightman |
| 8,088,790 B2 | 1/2012 | Kshirsagar |
| 8,541,438 B2 | 9/2013 | Stoermer |
| 8,673,932 B2 | 3/2014 | Kshirsagar |
| 8,691,837 B2 | 4/2014 | Krepski |
| 8,697,873 B2 | 4/2014 | Krepski |
| 9,006,264 B2 | 4/2015 | Stoermer |
| 9,034,336 B2 | 5/2015 | Ferguson |
| 9,242,980 B2 | 1/2016 | Wightman |
| 9,334,268 B2 | 5/2016 | Hoves |
| 9,447,097 B2 | 9/2016 | Hoves |
| 9,550,773 B2 | 1/2017 | Stoermer |
| 2003/0212092 A1 | 11/2003 | Heppner |
| 2017/0217960 A1 | 8/2017 | Ferguson |

FOREIGN PATENT DOCUMENTS

| | | |
|---|---|---|
| JP | H11-080156 | 3/1999 |
| WO | WO 2006-074003 | 7/2006 |
| WO | WO 2019-123178 | 6/2019 |
| WO | WO 2020-109898 | 6/2020 |

OTHER PUBLICATIONS

Berge, "Pharmaceutical Salts," 1977, Journal of Pharmaceutical Sciences, vol. 66, No. 1, pp. 1-19.
Braun, Org. Synth., Collective Volume, 1928, 8, 30.
Gubitz, "Chiral separation by chromatographic and electromigration techniques: A review", Biopharmaceutics and Drug Disposition, 2001, vol. 22, pp. 291-336.
Higuchi., "Prodrugs as Novel Delivery Systems", vol. 14, ACS Publications, Table of contents, 4 pages.
Katritsky, "Comprehensive Organic Functional Group Transformations", 2005, Pergamon Press, Oxford, vol. 1-6, Table of contents, 2 pages.
Mane, "Racemic drug resolution: a comprehensive guide", Analytical Methods, 2016, vol. 8, pp. 7567-7586.
O'Brien, "Investigation of the Alamar blue (resazurin) fluorescent dye for the assessment of mammalian cell cytotoxicity", European Journal of Biochemistry, 2000, vol. 267, No. 17, pp. 5421-5426.
Okamoto, "Chiral HPLC for efficient resolution of enantiomers", Chemical Society Reviews, 2008, vol. 37, pp. 2593-2608.
Remington, "Remington's Pharmaceutical Sciences", Mack Publishing, 1990, Ed.18, 5pages.

(Continued)

*Primary Examiner* — Niloofar Rahmani
(74) *Attorney, Agent, or Firm* — Jean A. Lown

(57) ABSTRACT

Imidazo[4,5-c]quinoline compounds having a substituent that is attached at the N-1 position by a branched group, single enantiomers of the compounds, pharmaceutical compositions containing the compounds, and methods of making the compounds are disclosed. Methods of use of the compounds as immune response modifiers, for inducing cytokine biosynthesis in humans and animals, and in the treatment of diseases including infectious and neoplastic diseases are also disclosed.

15 Claims, No Drawings

(56) References Cited

OTHER PUBLICATIONS

Roche, "Bioreversible Carriers in Drug Design—Table of contents", 1987, American Pharmaceutical Association and Pergamon Press, 4 pages.
Trost, Comprehensive Organic Synthesis, Pergamon Press, 1991, vol. 1-8, Table of contents, 39 pages.
Wuts, "Greene's Protective Groups in Organic Synthesis", John Wiley & Sons, New York, 2014, Table of contents, 7 pages.
International Search report for PCT International Application No. PCT/IB2019/051510 dated May 23, 2019, 4 pages.

* cited by examiner

SUBSTITUTED IMIDAZO[4,5-C]QUINOLINE COMPOUNDS WITH AN N-1 BRANCHED GROUP

CROSS REFERENCE TO RELATED APPLICATIONS

This application is a national stage filing under 35 U.S.C. 371 of PCT/IB2019/051510, filed Feb. 25, 2019, which claims the benefit of U.S. Provisional Patent Application No. 62/636,367, filed Feb. 28, 2018, the disclosure of which is incorporated by reference in its/their entirety herein.

BACKGROUND

Some drug compounds act by stimulating certain key aspects of the immune system, as well as by suppressing certain other aspects (e.g., U.S. Pat. No. 6,039,969 (Tomai et al.) and U.S. Pat. No. 6,200,592 (Tomai et al.)). These compounds are sometimes referred to as immune response modifiers (IRMs). Some IRM compounds are useful for treating viral diseases, neoplasias, and $T_H2$-mediated diseases. Some IRM compounds are useful as vaccine adjuvants.

IRM compounds have been reported based on the following bicyclic and tricyclic ring systems: 1H-imidazo[4,5-c] quinolin-4-amines (e.g., U.S. Pat. No. 4,689,338 (Gerster)); 1H-imidazo[4,5-c]pyridin-4-amines (e.g., U.S. Pat. No. 5,446,153 (Lindstrom et al.)); 1H-imidazo[4,5-c][1,5]naphthyidin-4-amines (e.g., U.S. Pat. No. 6,194,425 (Gerster et al.)); thiazolo[4,5-c]quinolone-4-amines and oxazolo[4,5-c] quinolone-4-amines (e.g., U.S. Pat. No. 6,110,929 (Gerster et al.)); 6,7,8,9-1H-tetrahydro-1H-imidazo[4,5-c]quinolin-4-amines (e.g., U.S. Pat. No. 5,352,784 (Nikolaides et al.)); 2H-pyrazolo[3,4-c]quinolone-4-amines (e.g., U.S. Pat. No. 7,544,697 (Hays et al.)); and N-1 and 2-substituted 1H-imidazo[4,5-c]quinolin-4-amines (e.g., U.S. Pat. No. 6,331,539 (Crooks et al.), U.S. Pat. No. 6,451,810 (Coleman et al.), U.S. Pat. No. 6,664,264 (Dellaria et al.), U.S. Pat. No. 8,691,837 (Krepski et al.), U.S. Pat. No. 8,088,790 (Kshirsagar et al.), U.S. Pat. No. 8,673,932 (Kshirsagar et al.), U.S. Pat. No. 8,697,873 (Krepski et al.), and U.S. Pat. No. 7,915,281 (Krepski et al.)).

SUMMARY

New compounds that can be useful in inducing cytokine biosynthesis in humans and animals are disclosed. Such compounds (or salts thereof) are of the following Formula (I):

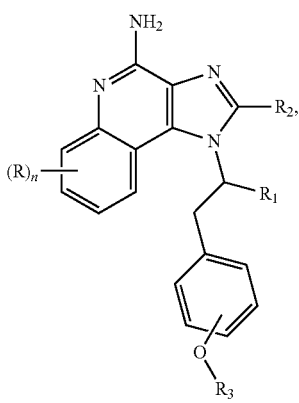

Formula (I)

wherein:
n is an integer of 0 or 1;
R is selected from the group consisting of halogen, hydroxy, alkyl, alkoxy, and —C(O)—O-alkyl;
$R_1$ is —$C_{1-3}$ alkylene-O—$C_{1-3}$ alkyl;
$R_2$ is selected from the group consisting of hydrogen, methyl, ethyl, n-propyl, n-butyl, —$CH_2OCH_3$, —$CH_2OCH_2CH_3$, and —$CH_2CH_2OCH_3$; and
$R_3$ is alkyl, aralkyl, wherein the alkyl or alkyl portion of the aralkyl can be optionally interrupted by one or more non-peroxidic —O— atoms, and wherein the aryl portion of the aralkyl can be optionally substituted with halogen, hydroxy, alkyl, alkoxy, or combinations thereof.

The compounds of Formula (I) have a chiral center in the branched group off N-1. Thus, the compounds of Formula (I) can be resolved into compounds (or salts thereof) of Formulas (II) and (III) (and/or such compounds can be synthesized using well-known techniques using chiral starting materials):

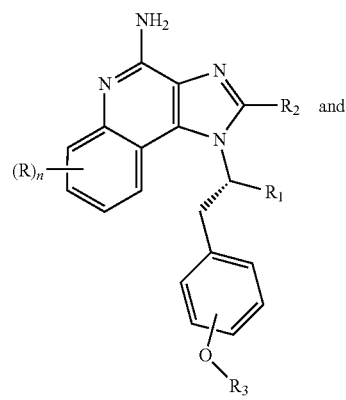

Formula (II)

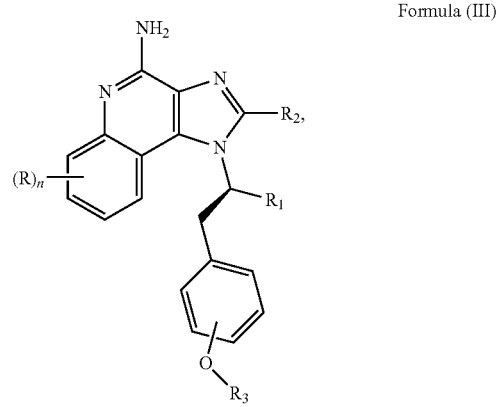

Formula (III)

wherein n, R, $R_1$, $R_2$, and $R_3$ are as defined above.

The compounds and salts, such as pharmaceutically acceptable salts, of these compounds can be used as immune response modifiers due to their ability to induce cytokine biosynthesis (e.g., induce the synthesis of at least one cytokine) and otherwise modulate the immune response when administered to humans or animals. The compounds can therefore be used in the treatment of a variety of conditions such as viral diseases and tumors that are responsive to such changes in the immune response. The compounds can also be used as vaccine adjuvants when administered in combination with a vaccine.

Pharmaceutical compositions containing an effective amount of a compound (or salts thereof including pharmaceutically acceptable salts thereof) of Formula (I), such as a compound of Formula (II), Formula (III), or a combination thereof, are disclosed.

Also disclosed are methods of inducing cytokine biosynthesis in a human or animal, treating a viral disease in a human or animal, and treating a neoplastic disease in a human or animal by administering to the human or animal a compound of Formula (I), such as a compound of Formula (II), Formula (III), or a combination thereof, and/or pharmaceutically acceptable salt thereof.

The term "alkyl" refers to a monovalent group that is a radical of an alkane and includes straight-chain, branched, cyclic, and bicyclic alkyl groups, and combinations thereof. Unless otherwise indicated, the alkyl groups typically contain from 1 to 20 carbon atoms. In some embodiments, the alkyl groups contain 1 to 10 carbon atoms, 1 to 6 carbon atoms, 1 to 4 carbon atoms, or 1 to 3 carbon atoms. Examples of "alkyl" groups include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, norbornyl, and the like.

The term "alkylene" refers to a divalent group that is a radical of an alkane and includes groups that are linear, branched, cyclic, bicyclic, or a combination thereof. Unless otherwise indicated, the alkylene group typically has 1 to 20 carbon atoms. In some embodiments, the alkylene group has 1 to 10 carbon atoms, 1 to 6 carbon atoms, or 1 to 4 carbon atoms. Examples of "alkylene" groups include methylene, ethylene, 1,3-propylene, 1,2-propylene, 1,4-butylene, 1,4-cyclohexylene, and 1,4-cyclohexyldimethylene.

An alkyl or alkylene group with carbon atoms optionally "interrupted" by one or more non-peroxidic —O— atoms refers to having carbon atoms on either side of the —O—. Examples include —CH$_2$CH$_2$—O—CH$_2$CH$_2$—, —CH$_2$—CH$_2$—O—CH$_2$—CH$_2$—O—CH$_2$CH$_2$—, —(CH$_2$)$_{2-4}$—(OCH$_2$CH$_2$-)$_{1-5}$, —(CH$_2$)$_{2-6}$—(OCH$_2$CH$_2$-)$_{1-4}$, and the like.

The term "alkoxy" refers to a monovalent group having an oxy group bonded directly to an alkyl group.

The term "$C_{x-y}$alkyl," "$C_{x-y}$alkoxy," and "$C_{x-y}$alkylene" are inclusive of straight chain groups, branched chain groups, cyclic groups, and combinations thereof that have X to Y carbon atoms. For example, a "$C_{1-5}$alkyl" includes alkyl groups of 1 carbon, 2 carbons, 3 carbons, 4 carbons, and 5 carbons. Some examples of "$C_{1-5}$alkyl" include methyl, ethyl, n-propyl, isopropyl, n-butyl, sec-butyl, isobutyl, isomeric pentyls, cyclopropyl, cyclopentyl, and —CH$_2$-cyclopropyl.

The term "aryl" refers to a monovalent group that is aromatic and, optionally, carbocyclic. The aryl has at least one aromatic ring. Any additional rings can be unsaturated, partially saturated, saturated, or aromatic. Optionally, the aromatic ring can have one or more additional carbocyclic rings that are fused to the aromatic ring. Unless otherwise indicated, the aryl groups typically contain from 6 to 20 carbon atoms. In some embodiments, the aryl groups contain 6 to 18, 6 to 16, 6 to 12, or 6 to 10 carbon atoms. Examples of an aryl group include phenyl (designated by the abbreviation "Ph" herein), naphthyl, biphenyl, phenanthryl, and anthracyl.

The term "aralkyl" refers to a monovalent group that is an alkyl group substituted with an aryl group (e.g., as in a benzyl group). Unless otherwise indicated, for both groups, the alkyl portion, which can be considered to be an alkylene group, often has 1 to 10 carbon atoms, 1 to 6 carbon atoms, or 1 to 4 carbon atoms and an aryl portion often has 6 to 20 carbon atoms, 6 to 18 carbon atoms, 6 to 16 carbon atoms, 6 to 12 carbon atoms, or 6 to 10 carbon atoms.

The "salt" of a compound includes pharmaceutically acceptable salts, such as those described in Berge, Stephen M., "Pharmaceutical Salts," *Journal of Pharmaceutical Sciences*, 1977, 66, pages 1-19. For example, salts can be prepared by reacting a free base compound (that is, one not in a salt form) with an inorganic or organic acid such as, for example, hydrochloric acid, sulfuric acid, hydrobromic acid, methane sulfonic acid, ethane sulfonic acid, malic acid, maleic acid, acetic acid, trifluoroacetic acid, para-toluenesulfonic acid, salicylic acid, succinic acid, tartaric acid, citric acid, pamoic acid, xinafoic acid, oxalic acid, and the like.

As used herein, "pharmaceutically acceptable carriers" include those carriers that can deliver therapeutically or prophylactically effective amounts of one or more of the compounds or salts of the disclosure to a subject by a chosen route of administration, are generally tolerated by the subject, and have an acceptable toxicity profile (preferably minimal to no toxicity at an administered dose). Some suitable pharmaceutically acceptable carriers are described in Remington's Pharmaceutical Sciences, 18$^{th}$ Edition (1990), Mack Publishing Co., and can be readily selected by one of ordinary skill in the art. Typical pharmaceutically acceptable salts include hydrochloride and dihydrochloride.

"Effective amount" (including "therapeutically effective amount" and "prophylactically effective amount") are defined as an amount of compound or salt sufficient to induce a therapeutic or prophylactic effect, such as cytokine induction, immunomodulation, antitumor activity, and/or antiviral activity. Depending on the disease or condition, the desired cytokine profile, and/or the acceptable level of side effects, the effective amount may vary. For example, a small amount of a very active compound or salt, or a large amount of a compound or salt of low activity, may be used to avoid undesirable side effects.

"Treat" and "Treatment" as well as variations thereof refer to reducing, limiting progression, ameliorating, preventing, or resolving to any extent the symptoms or signs related to a condition.

"Ameliorate" and "ameliorating" refers to any reduction in the extent, severity, frequency, and/or likelihood of a symptom or clinical characteristic of a particular disease or condition.

"Antigen" refers to any substance that can be bound by an antibody in a manner that is immunospecific to some degree.

Herein, the term "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements. Any of the elements or combinations of elements that are recited in this specification in open-ended language (e.g., comprise and derivatives thereof), are considered to additionally be recited in closed-ended language (e.g., consist and derivatives thereof) and in partially closed-ended language (e.g., consist essentially, and derivatives thereof).

The words "preferred" and "preferably" refer to embodiments of the disclosure that may afford certain benefits, under certain circumstances. However, other claims may also be preferred, under the same or other circumstances. Furthermore, the recitation of one or more preferred claims does not imply that other claims are not useful and is not intended to exclude other claims from the scope of the disclosure.

In this application, terms such as "a," "an," and "the" are not intended to refer to only a singular entity but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

Also, herein, all numbers are assumed to be modified by the term "about" and in certain embodiments, preferably, by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also, herein, the recitations of numerical ranges by endpoints include all numbers subsumed within that range as well as the endpoints (e.g., 1 to 5 includes 1, 1.5, 2, 2.75, 3, 3.80, 4, 5, etc.).

As used herein, the terms "ambient temperature" or "room temperature" refers to a temperature of 20° C. to 25° C. or 22° C. to 25° C.

The term "in the range" or "within a range" (and similar statements) includes the endpoints of the stated range.

Groupings of alternative elements or embodiments disclosed herein are not to be construed as limitations. Each group member may be referred to and claimed individually or in any combination with other members of the group or other elements found therein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

When a group is present more than once in a formula described herein, each group is "independently" selected, whether specifically stated or not. For example, when more than one R group is present in a formula, each R group is independently selected.

Reference throughout this specification to "one embodiment," "an embodiment," "certain embodiments," or "some embodiments," etc., means that a particular feature, configuration, composition, or characteristic described in connection with the embodiment is included in at least one embodiment of the invention. Thus, the appearances of such phrases in various places throughout this specification are not necessarily referring to the same embodiment of the invention. Furthermore, the particular features, configurations, compositions, or characteristics may be combined in any suitable manner in one or more embodiments.

The above summary of the present disclosure is not intended to describe each disclosed embodiment or every implementation of the present invention. The description that follows more particularly exemplifies illustrative embodiments. In several places throughout the application, guidance is provided through lists of examples, which examples may be used in various combinations. In each instance, the recited list serves only as a representative group and should not be interpreted as an exclusive list. Thus, the scope of the present disclosure should not be limited to the specific illustrative structures described herein, but rather extends at least to the structures described by the language of the claims, and the equivalents of those structures. Any of the elements that are positively recited in this specification as alternatives may be explicitly included in the claims or excluded from the claims, in any combination as desired. Although various theories and possible mechanisms may have been discussed herein, in no event should such discussions serve to limit the claimable subject matter.

DETAILED DESCRIPTION OF ILLUSTRATIVE EMBODIMENTS

This disclosure provides compounds (or salts thereof) of the following Formula (I):

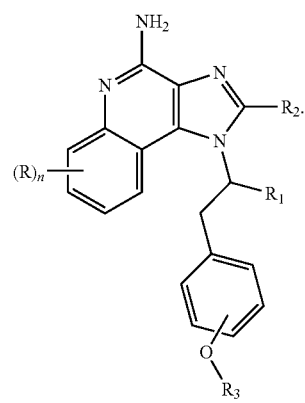

Formula (I)

The compounds of Formula (I) have a chiral center in the branched group off N–1. Thus, the compounds of Formula (I) can be resolved into compounds (or salts thereof) of Formulas (II) and (III):

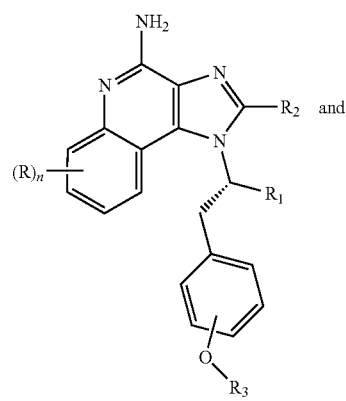

Formula (II)

and

-continued

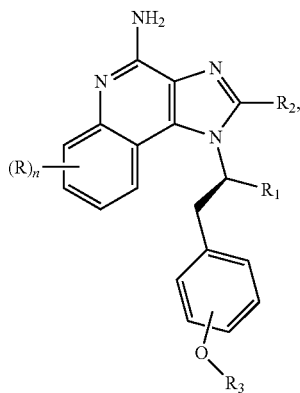

Formula (III)

wherein:
n is an integer of 0 or 1;
R is selected from the group consisting of halogen, hydroxy, alkyl, alkoxy, and —C(O)—O-alkyl;
$R_1$ is —$C_{1-3}$ alkylene-O—$C_{1-3}$ alkyl;
$R_2$ is selected from the group consisting of hydrogen, methyl, ethyl, n-propyl, n-butyl, —$CH_2OCH_3$, —$CH_2OCH_2CH_3$, and —$CH_2CH_2OCH_3$; and
$R_3$ is alkyl, aralkyl, wherein the alkyl or alkyl portion of the aralkyl can be optionally interrupted by one or more non-peroxidic —O— atoms, and wherein the aryl portion of the aralkyl can be optionally substituted with halogen, hydroxy, alkyl, alkoxy, or combinations thereof.

Depending on the disease or condition, the desired cytokine profile, and/or the acceptable level of side effects, a compound or salt of Formula (II) may be more desirable than a compound or salt of Formula (III). Typically, compounds or salts of Formula (II) are more active with respect to inducing cytokine biosynthesis than compounds or salts of Formula (III). Whereas, generally a more active compound or salt of Formula (II) would be desirable for use, a less active compound or salt of Formula (III) may be used in certain situations, for example, to avoid undesirable side effects.

In some embodiments of Formulas (I), (II), and (III), the —O—$R_3$ group is in a meta or para position, whereas in some embodiments, the —O—$R_3$ group is in the para position.

In some embodiments of Formulas (I), (II), and (III), R is selected from the group consisting of halogen, hydroxy, —$C_{1-7}$ alkoxy, and —C(O)—O—$C_{1-5}$alkyl. In some embodiments, R is selected from the group consisting of hydroxy, F, and Cl. In some embodiments, R is selected from the group consisting of F and Cl.

In some embodiments of Formulas (I), (II), and (III), n is 0.

In some embodiments of Formulas (I), (II), and (III), $R_1$ is —$CH_2OCH_3$ or —$CH_2OCH_2CH_3$. In some embodiments, $R_1$ is —$CH_2OCH_2CH_3$.

In some embodiments of Formulas (I), (II), and (III), $R_2$ is selected from the group consisting of hydrogen, methyl, and ethyl. In some embodiments, $R_2$ is hydrogen or methyl.

In some embodiments of Formulas (I), (II), and (III), $R_3$ has at least 4, at least 5, or at least 6 carbon atoms.

In some embodiments of Formulas (I), (II), and (III), $R_3$ has up to 18, up to 16, or up to 14 carbon atoms. In some embodiments, $R_3$ has up to 12 carbon atoms.

In some embodiments of Formulas (I), (II), and (III), $R_3$ is an alkyl, optionally interrupted by non-peroxidic —O— atoms. In some embodiments, $R_3$ is an alkyl not interrupted by —O— atoms.

In some embodiments of Formulas (I), (II), and (III), $R_3$ is a linear alkyl. In some embodiments, $R_3$ is selected from the group consisting of —$(CH_2)_3CH_3$, —$(CH_2)_4CH_3$, —$(CH_2)_5CH_3$, —$(CH_2)_6CH_3$, —$(CH_2)_7CH_3$, and —$(CH_2)_{11}CH_3$. In some embodiments, $R_3$ is selected from the group consisting of —$(CH_2)_3CH_3$, —$(CH_2)_5CH_3$, —$(CH_2)_7CH_3$, and —$(CH_2)_{11}CH_3$. In some embodiments, $R_3$ is —$(CH_2)_3CH_3$. In some embodiments, $R_3$ is —$(CH_2)_5CH_3$. In some embodiments, $R_3$ is —$(CH_2)_7CH_3$. In some embodiments, $R_3$ is —$(CH_2) CH_3$.

In some embodiments of Formulas (I), (II), and (III), $R_3$ is a branched alkyl. In some embodiments, $R_3$ is —$CH_2$—$CH(CH_2CH_3)$—$(CH_2)_3CH_3$.

In some embodiments of Formulas (I), (II), and (III), $R_3$ is an aralkyl, wherein the alkyl portion is optionally interrupted by non-peroxidic —O— atoms. In some embodiments, $R_3$ is an aralkyl having an alkyl not interrupted by —O— atoms. In some embodiments, $R_3$ is —$CH_2$-phenyl.

In some embodiments of Formulas (I), (II), and (III), $R_1$ is —$C_{1-3}$ alkylene-O—$C_{1-3}$ alkyl; $R_2$ is selected from the group consisting of hydrogen, methyl, and ethyl; $R_3$ is —$C_{4-12}$alkyl; and n is 0.

In some embodiments of Formulas (I), (II), and (III), $R_1$ is —$CH_2OCH_3$ or —$CH_2OCH_2CH_3$; $R_2$ is selected from the group consisting of hydrogen, methyl, and ethyl; $R_3$ is —$C_{4-12}$alkyl; and n is 0. In some embodiments of these compounds or salts thereof, $R_2$ is hydrogen. In some embodiments of these compounds or salts thereof, $R_3$ is selected from the group consisting of —$(CH_2)_3CH_3$, —$(CH_2)_4CH_3$, —$(CH_2)_5CH_3$, —$(CH_2)_6CH_3$, —$(CH_2)_7CH_3$, and —$(CH_2)_{11}CH_3$. In some embodiments of these compounds or salts thereof, $R_3$ is selected from the group consisting of —$(CH_2)_3CH_3$, —$(CH_2)_5CH_3$, —$(CH_2)_7CH_3$, and —$(CH_2)_{11}CH_3$. In some embodiments of these compounds or salts thereof, $R_3$ is —$(CH_2)_3CH_3$, which can be 1-[(1S)-1-[(4-butoxyphenyl)methyl]-2-ethoxy-ethyl]imidazo[4,5-c]quinolin-4-amine. In some embodiments of these compounds or salts thereof, $R_3$ is —$(CH_2)_5CH_3$, which can be 1-[(1S)-1-(ethoxymethyl)-2-(4-hexoxyphenyl)ethyl]imidazo[4,5-c]quinolin-4-amine. In some embodiments of these compounds or salts thereof, $R_3$ is —$(CH_2)_7CH_3$, which can be 1-[(1S)-1-(ethoxymethyl)-2-(4-octoxyphenyl)ethyl]imidazo[4,5-c]quinolin-4-amine. In some embodiments of these compounds or salts thereof, $R_3$ is —$(CH_2)_{11}CH_3$, which can be 1-[(1S)-1-[(4-dodecoxyphenyl)methyl]-2-ethoxy-ethyl]imidazo[4,5-c]quinolin-4-amine.

In some embodiments of Formulas (I), (II), and (III), the compound is present in the form of a salt. The salt is typically a pharmaceutically acceptable salt. Most commonly the salt is a hydrochloride salt.

In some embodiments, mixtures of compounds of Formulas (II) and (III) are present. In some embodiments, the compound of Formula (II) has an enantiomeric purity of at least 80% enantiomeric excess (80% ee). The enantiomeric purity of a compound of Formula (II) is relative to a compound of Formula (III). In some embodiments, the compound of Formula (II) has an enantiomeric purity of at least 90% enantiomeric excess (90% ee). In some embodiments, the compound of Formula (II) has an enantiomeric purity of at least 95% enantiomeric excess (95% ee). In some embodiments, the compound of Formula (II) has an enantiomeric purity of at least 97% enantiomeric excess (97% ee). In some embodiments, the compound of Formula (II) has an enantiomeric purity of at least 98% enantiomeric excess (98% ee). In some embodiments, the compound of Formula (II) has an enantiomeric purity of at least 99% enantiomeric excess (99% ee). In some embodiments, the compound of Formula (II) has an enantiomeric purity of at least 99.5% enantiomeric excess (99.5% ee). In some embodiments, the compound of Formula (II) has an enantiomeric purity of at least 99.8% enantiomeric excess (99.8% ee).

Exemplary compounds of Formulas (I), (II), and (III) are presented in Tables 1-6. In the Tables 1-6, each row represents a specific compound with n, $R_1$, $R_2$, and $R_3$ defined.

TABLE 1

| n | $R_1$ | $R_2$ | $R_3$ |
|---|---|---|---|
| 0 | —$CH_2OCH_3$ | H | —$(CH_2)_3CH_3$ |
| 0 | —$CH_2OCH_3$ | H | —$(CH_2)_4CH_3$ |
| 0 | —$CH_2OCH_3$ | H | —$(CH_2)_5CH_3$ |
| 0 | —$CH_2OCH_3$ | H | —$(CH_2)_6CH_3$ |
| 0 | —$CH_2OCH_3$ | H | —$(CH_2)_7CH_3$ |
| 0 | —$CH_2OCH_3$ | H | —$(CH_2)_{11}CH_3$ |
| 0 | —$CH_2OCH_3$ | H | —$CH_2$—$CH(CH_2CH_3)$—$(CH_2)_3CH_3$ |
| 0 | —$CH_2OCH_3$ | H | —$CH_2$-phenyl |

TABLE 2

| n | $R_1$ | $R_2$ | $R_3$ |
|---|---|---|---|
| 0 | —$CH_2OCH_3$ | —$CH_3$ | —$(CH_2)_3CH_3$ |
| 0 | —$CH_2OCH_3$ | —$CH_3$ | —$(CH_2)_4CH_3$ |
| 0 | —$CH_2OCH_3$ | —$CH_3$ | —$(CH_2)_5CH_3$ |
| 0 | —$CH_2OCH_3$ | —$CH_3$ | —$(CH_2)_6CH_3$ |
| 0 | —$CH_2OCH_3$ | —$CH_3$ | —$(CH_2)_7CH_3$ |
| 0 | —$CH_2OCH_3$ | —$CH_3$ | —$(CH_2)_{11}CH_3$ |
| 0 | —$CH_2OCH_3$ | —$CH_3$ | —$CH_2$—$CH(CH_2CH_3)$—$(CH_2)_3CH_3$ |
| 0 | —$CH_2OCH_3$ | —$CH_3$ | —$CH_2$-phenyl |

TABLE 3

| n | $R_1$ | $R_2$ | $R_3$ |
|---|---|---|---|
| 0 | —$CH_2OCH_3$ | —$CH_2CH_3$ | —$(CH_2)_3CH_3$ |
| 0 | —$CH_2OCH_3$ | —$CH_2CH_3$ | —$(CH_2)_4CH_3$ |
| 0 | —$CH_2OCH_3$ | —$CH_2CH_3$ | —$(CH_2)_5CH_3$ |
| 0 | —$CH_2OCH_3$ | —$CH_2CH_3$ | —$(CH_2)_6CH_3$ |
| 0 | —$CH_2OCH_3$ | —$CH_2CH_3$ | —$(CH_2)_7CH_3$ |
| 0 | —$CH_2OCH_3$ | —$CH_2CH_3$ | —$(CH_2)_{11}CH_3$ |
| 0 | —$CH_2OCH_3$ | —$CH_2CH_3$ | —$CH_2$—$CH(CH_2CH_3)$—$(CH_2)_3CH_3$ |
| 0 | —$CH_2OCH_3$ | —$CH_2CH_3$ | —$CH_2$-phenyl |

TABLE 4

| n | $R_1$ | $R_2$ | $R_3$ |
|---|---|---|---|
| 0 | —$CH_2OCH_2CH_3$ | H | —$(CH_2)_3CH_3$ |
| 0 | —$CH_2OCH_2CH_3$ | H | —$(CH_2)_4CH_3$ |
| 0 | —$CH_2OCH_2CH_3$ | H | —$(CH_2)_5CH_3$ |
| 0 | —$CH_2OCH_2CH_3$ | H | —$(CH_2)_6CH_3$ |
| 0 | —$CH_2OCH_2CH_3$ | H | —$(CH_2)_7CH_3$ |
| 0 | —$CH_2OCH_2CH_3$ | H | —$(CH_2)_{11}CH_3$ |
| 0 | —$CH_2OCH_2CH_3$ | H | —$CH_2$—$CH(CH_2CH_3)$—$(CH_2)_3CH_3$ |
| 0 | —$CH_2OCH_2CH_3$ | H | —$CH_2$-phenyl |

TABLE 5

| n | $R_1$ | $R_2$ | $R_3$ |
|---|---|---|---|
| 0 | —$CH_2OCH_2CH_3$ | —$CH_3$ | —$(CH_2)_3CH_3$ |
| 0 | —$CH_2OCH_2CH_3$ | —$CH_3$ | —$(CH_2)_4CH_3$ |
| 0 | —$CH_2OCH_2CH_3$ | —$CH_3$ | —$(CH_2)_5CH_3$ |
| 0 | —$CH_2OCH_2CH_3$ | —$CH_3$ | —$(CH_2)_6CH_3$ |
| 0 | —$CH_2OCH_2CH_3$ | —$CH_3$ | —$(CH_2)_7CH_3$ |
| 0 | —$CH_2OCH_2CH_3$ | —$CH_3$ | —$(CH_2)_{11}CH_3$ |
| 0 | —$CH_2OCH_2CH_3$ | —$CH_3$ | —$CH_2$—$CH(CH_2CH_3)$—$(CH_2)_3CH_3$ |
| 0 | —$CH_2OCH_2CH_3$ | —$CH_3$ | —$CH_2$-phenyl |

TABLE 6

| n | $R_1$ | $R_2$ | $R_3$ |
|---|---|---|---|
| 0 | —$CH_2OCH_2CH_3$ | —$CH_2CH_3$ | —$(CH_2)_3CH_3$ |
| 0 | —$CH_2OCH_2CH_3$ | —$CH_2CH_3$ | —$(CH_2)_4CH_3$ |
| 0 | —$CH_2OCH_2CH_3$ | —$CH_2CH_3$ | —$(CH_2)_5CH_3$ |
| 0 | —$CH_2OCH_2CH_3$ | —$CH_2CH_3$ | —$(CH_2)_6CH_3$ |
| 0 | —$CH_2OCH_2CH_3$ | —$CH_2CH_3$ | —$(CH_2)_7CH_3$ |
| 0 | —$CH_2OCH_2CH_3$ | —$CH_2CH_3$ | —$(CH_2)_{11}CH_3$ |
| 0 | —$CH_2OCH_2CH_3$ | —$CH_2CH_3$ | —$CH_2$—$CH(CH_2CH_3)$—$(CH_2)_3CH_3$ |
| 0 | —$CH_2OCH_2CH_3$ | —$CH_2CH_3$ | —$CH_2$-phenyl |

The disclosure provides a method of inducing cytokine biosynthesis in a human or animal by administering to the human or animal an effective amount of a compound or salt selected from the group consisting of any one of the above embodiments of Formula (I), which may be compounds of Formula (II) and/or Formula (III), or salts thereof.

The disclosure provides a method of inducing IFN-alpha biosynthesis in a human or animal by administering to the human or animal an effective amount of a compound or salt selected from any one of the above embodiments of Formula (I), which may be compounds of Formula (II) and/or Formula (III), or salts thereof.

The disclosure provides a method of inducing IFN-gamma biosynthesis in a human or animal by administering to the human or animal an effective amount of a compound or salt selected from any one of the above embodiments of Formula (I), which may be compounds of Formula (II) and/or Formula (III), or salts thereof.

The disclosure provides a method of inducing TNF-alpha biosynthesis in a human or animal by administering to the human or animal an effective amount of a compound or salt selected from any one of the above embodiments of Formula (I), which may be compounds of Formula (II) and/or Formula (III), or salts thereof.

The disclosure provides a method of inducing IP-10 biosynthesis in a human or animal by administering to the human or animal an effective amount of a compound or salt selected from any one of the above embodiments of Formula (I), which may be compounds of Formula (II) and/or Formula (III), or salts thereof.

The disclosure provides a method for treating a viral disease in a human or animal by administering to the human or animal an effective amount of a compound or salt selected from any one of the above embodiments of Formula (I), which may be compounds of Formula (II) and/or Formula (III), or salts thereof.

The disclosure provides a method for treating a neoplastic disease in a human or animal by administering to the human or animal an effective amount of a compound or salt selected from any one of the above embodiments of Formula (I), which may be compounds of Formula (II) and/or Formula (III), or salts thereof.

The compounds of the disclosure may be synthesized by synthetic routes that include processes analogous to those well known in the chemical arts, particularly in light of the description contained herein. The starting materials are generally available from commercial sources such as the Sigma-Aldrich Company (St. Louis, Mo.) or are readily prepared using methods well known to those of ordinary skill in the art (e.g., prepared by methods generally described in Louis F. Fieser and Mary Fieser, Reagents for Organic Synthesis, v. 1-26, Wiley, New York; Alan R Katritsky, Otto Meth-Cohn, Charles W. Rees, Comprehensive Organic Functional Group Transformations, volume 1-6, Pergamon Press, Oxford, England, (1995); Barry M. Trost and Ian Fleming, Comprehensive Organic Synthesis, v. 1-8, Pergamon Press, Oxford, England, (1991); or Beilsteins Handbuch der Organischen Chemie, 4, Aufl. Ed. Springer-Verlag, Berlin, Germany, including supplements (also available via the Beilstein online database)).

Compounds of the disclosure can be prepared, for example, according to Reaction Schemes I and II where R, $R_2$, $R_3$, and n are as described above. In step (1) of Reaction Scheme I, 2-(tert-butoxycarbonylamino)-3-(4-tert-butoxyphenyl)propanoic acid of Formula (IV) (a di-protected version of tyrosine) can be can be reacted with isobutyl chloroformate and N-methylmorpholine followed by reaction with sodium borohydride in step (2) to provide the alcohol of Formula (V). Alkylation of the alcohol of Formula (V) in step (3) with an alkylating agent such as for example dialkylsulfate or an alkyl halide can provide the alkyl ether of Formula (VI). In step (4) of Reaction Scheme I, the protecting groups can be removed from the compound of Formula (VI) using concentrated hydrochloric acid in ethanol with heating to provide the compound of Formula (VII).

In Reaction Scheme II, a 4-chloro-3-nitroquinoline of Formula (VIII) is reacted in step (5) with the compound of Formula (VII) to provide a 3-nitroquinolin-4-amine of Formula (IX). The reaction can be carried out by adding the amine of Formula (VII) to a solution of Formula (VIII) in a suitable solvent such as dichloromethane in the presence of a tertiary amine such as triethylamine. The 4-chloro-3-nitroquinoline compound of Formula (VIII) and substituted analogs are known compounds (see, for example, U.S. Pat. No. 3,700,674 (Diehl et al.), U.S. Pat. No. 5,389,640 (Gerster et al.), U.S. Pat. No. 6,110,929 (Gerster et al.), U.S. Pat. No. 7,923,560 (Wightman et al.), and references cited therein). In many cases, substituted analogs of Formula (VIII) (for example, n=1 and R being a halogen, alkoxy, or benzyloxy group) can be prepared starting with commercially available substituted anilines.

In step (6) of Reaction Scheme II, the nitro group of Formula (IX) can be reduced to an amino group. The reduction can be carried out in a pressure bottle using hydrogen, a catalytic amount of palladium or platinum on carbon, and a solvent such as methanol, acetonitrile, toluene, or combinations thereof. The reaction can be carried out with a Parr apparatus. In step (7) of Reaction Scheme II, the resulting 3,4-diamine compound can be reacted with a carboxylic acid ($R_2CO_2H$) to provide a 1H-imidazo[4,5-c]quinoline of Formula (X). Suitable equivalents to carboxylic acids such as acyl chlorides, thioesters, and 1,1-dialkoxyalkyl alkanoates can also be used. The carboxylic acid or equivalent is selected so that it will provide the desired $R_2$ substituent in a compound of Formula (X). For example, triethylorthoformate will provide a compound where $R_2$ is hydrogen and trimethyl orthovalerate will provide a compound where $R_2$ is n-butyl. The reaction can be carried out without a solvent or with an inert solvent. Optionally, a catalyst such as pyridine hydrochloride can be included.

In step (8) of Reaction Scheme II, the 1H-imidazo[4,5-c]quinoline-4-amine of Formula (X) is converted to an ether of Formula (XI) using conventional synthetic methods. For example, the compound of Formula (X) can be reacted with a suitable alkyl halide (alkyl bromide or alkyl chloride) and a base (such as cesium carbonate) in an inert solvent (such as N,N-dimethylformamide). The alkyl halide is selected so that it will provide the desired $R_3$ substituent in the compound of Formula (XI).

In step (9) of Reaction Scheme II, the 1H-imidazo[4,5-c]quinoline of Formula (XI) can be oxidized to provide a 1H-imidazo[4,5-c]quinoline-5N-oxide using a conventional oxidizing agent capable of forming an N-oxide. Preferably, a solution of the compound of Formula (XI) in a suitable solvent such as chloroform or dichloromethane is reacted with 3-chloroperbenzoic acid at ambient temperature.

In step (10) of Reaction Scheme II, the N-oxide compound can be aminated to provide a 1H-imidazo[4,5-c]quinoline-4-amine of Formula (XII). Step (10) involves reacting the N-oxide compound with a sulfonylating agent and an aminating agent in an inert solvent such as dichloromethane or chloroform. Suitable asulfonylating agents include alkyl- or arylsulfonyl chlorides such as benzenesulfonyl chloride, methanesulfonyl chloride, or para-toluenesulfonyl chloride. Ammonium hydroxide is a suitable aminating agent. Formula (XII) is an embodiment of Formula (I).

Reaction Scheme I

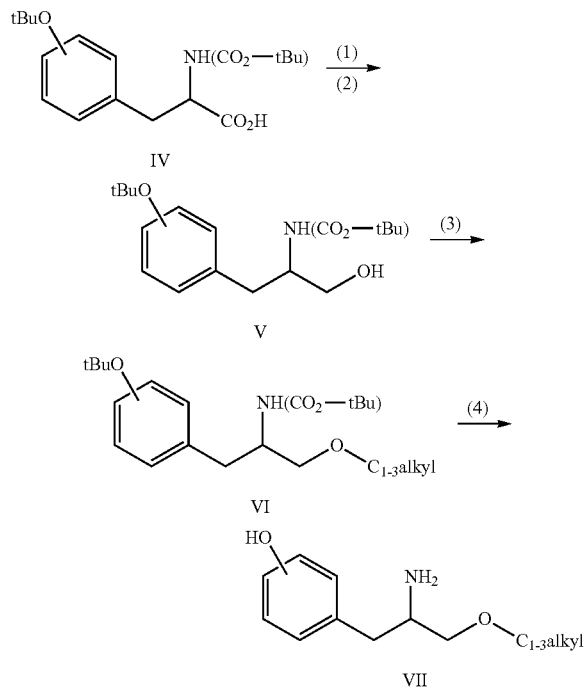

Reaction Scheme II

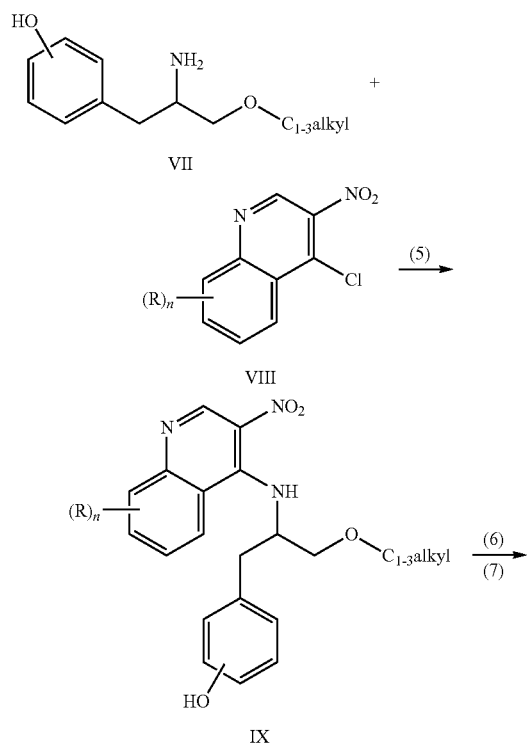

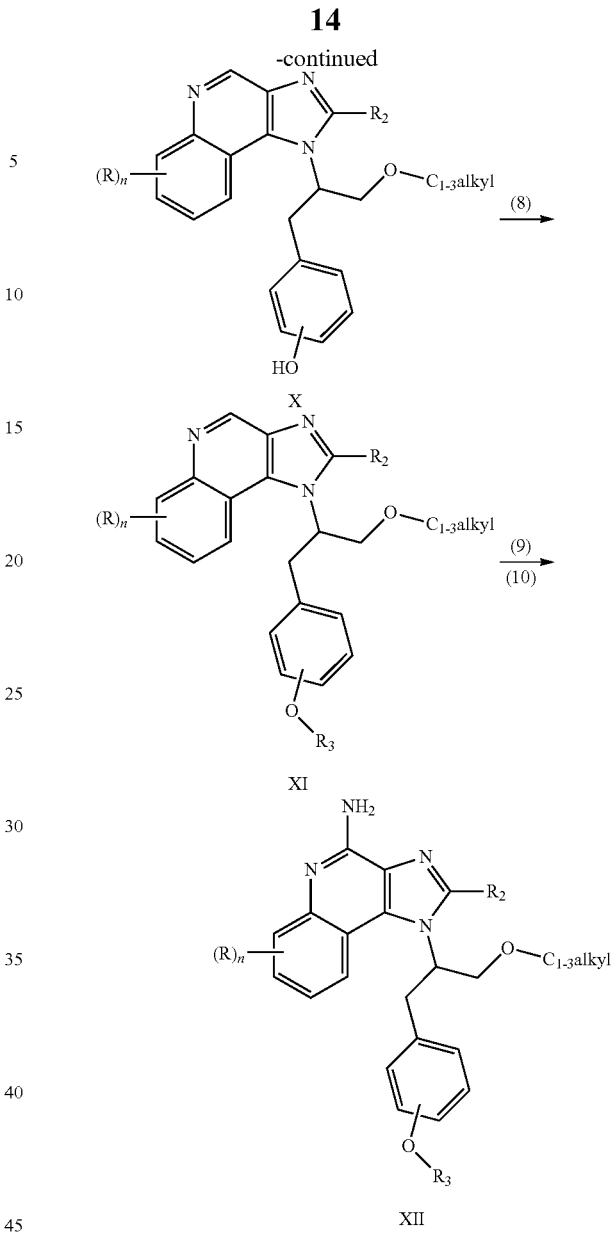

Compounds of the disclosure can be prepared according to Reaction Schemes I and II with the starting compound of Formula (IV) being replaced with similarly di-protected versions of homotyrosine, 3-amino-4-(3-hydroxyphenyl)butanoic acid, 4-amino-5-(4-hydroxyphenyl)pentanoic acid, or 4-amino-5-(3-hydroxyphenyl)pentanoic acid.

Compounds of Formula (I), which may be compounds of Formula (II) and/or Formula (III), can be prepared by starting the reaction scheme with reactants having high enantiomeric purity. Alternatively, a racemic mixture of reactants or reactants of low enantiomeric purity (for example 10-70% enantiomeric excess) can be used with the final product isolated as the desired Formula (II) enantiomer using any suitable procedure for the resolution of a mixture of enantiomers. A well-known method for the resolution of a mixture of enantiomers is HPLC chromatography using a column with a chiral stationary phase (CSP). Another standard method for the resolution of a mixture of enantiomers involves reacting the mixture with an optically pure carboxylic acid to form diastereomeric salts that can be readily separated by for example recrystallization or chromatography methods. Regeneration of the free base completes the resolution process. Examples of resolving agents that are available in high enantiomeric purity include, but are not limited to, (+)-tartaric acid, (−)-mandelic acid, (−)-malic acid, (+)-camphor-10-sulfonic acid, and (+)-2,3-dibenzoyl-tartaric acid. If needed, different types of resolution steps can be combined, and multiple resolution steps can be utilized to achieve the desired enantiomeric purity. The enantiomeric purity is represented as the percent enantiomeric excess (% ee). Methods for the resolution of isomers are described in the references: Y. Okamoto, Chemical Society Reviews, 2008, 37, pages 2593-2608; G. Gubitz, Biopharmaceutics and Drug Disposition, 2001, 22, pages 291-336; and S. Mane, Analytical Methods, 2016, 8, pages 7567-7586.

In the preparation of the compounds of the disclosure it is understood by one of ordinary skill in the art that it may be necessary to protect a particular functional group while reacting other functional groups of an intermediate compound. The need for such protection will vary depending on the nature of the particular functional group and the conditions of the particular reaction step. A review of reactions for protecting and deprotecting functional groups can be found in P. G. M. Wuts, Greene's Protective Groups in Organic Synthesis, John Wiley & Sons, New York, USA, 2014.

Conventional methods and techniques of separation and purification can be used to isolate the IRM compounds used in the compositions of the disclosure. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

The enantiomeric excess of the compounds of the disclosure can be determined using standard analytical assays such as gas chromatography or HPLC with a column having a chiral stationary phase (CSP). Suitable columns with a CSP are available from Chiral Technologies, Inc., Westchester, Pa.

Enantiomeric excess (% ee) is calculated according to Equation 1.

$$\text{enantiomeric excess (\% } ee) = \frac{\left(\begin{array}{c}\text{mole \% of}\\ \text{major enantiomer}\end{array}\right) - \left(\begin{array}{c}\text{mol \% of}\\ \text{minor enatiomer}\end{array}\right)}{\left(\begin{array}{c}\text{mole \% of}\\ \text{major enantiomer}\end{array}\right) + \left(\begin{array}{c}\text{mole \% of}\\ \text{minor enantiomer}\end{array}\right)} \times 100. \quad \text{Equation 1}$$

Enantiomeric excess (% ee) can be calculated from a chiral HPLC chromatogram by comparing the peak areas of the major enantiomer and minor enantiomer signals according to Equation 2.

$$\text{enantiomeric excess (\% } ee) = \frac{\left(\begin{array}{c}\text{peak area of}\\ \text{major enantiomer}\end{array}\right) - \left(\begin{array}{c}\text{peak area of}\\ \text{minor enatiomer}\end{array}\right)}{\left(\begin{array}{c}\text{peak area of}\\ \text{major enantiomer}\end{array}\right) + \left(\begin{array}{c}\text{peak area of}\\ \text{minor enantiomer}\end{array}\right)} \times 100. \quad \text{Equation 2}$$

Prodrugs of the disclosed compounds can also be prepared by attaching to the compounds a functional group that can be cleaved under physiological conditions. Typically, a cleavable functional group will be cleaved in vivo by various mechanisms (such a through a chemical (e.g., hydrolysis) or enzymatic transformation) to yield a compound of the disclosure. A discussion of the use of prodrugs is provided by T. Higuchi and W. Stella, "Prodrugs as Novel Delivery Systems", vol. 14 of the ACS Symposium Series; and in Bioreversible Carriers in Drug Design, ed. Edward B. Roche, American Pharmaceutical Association and Pergamon Press, 1987.

Pharmaceutical Compositions and Biological Activity

Pharmaceutical compositions of the disclosure are also contemplated. Pharmaceutical compositions of the disclosure contain a therapeutically effective amount of a compound or salt of the disclosure (described herein) in combination with a pharmaceutically acceptable carrier.

The compounds of Formula (I), which may be compounds of Formula (II) and/or Formula (III), may be provided in any pharmaceutical composition suitable for administration to a subject (human or animal) and may be present in the pharmaceutical composition in any suitable form (for example as a solution, a suspension, an emulsion, or any form of a mixture). The pharmaceutical composition may be formulated with any pharmaceutically acceptable excipient, carrier, or vehicle. In some embodiments, the pharmaceutically acceptable carrier comprises water (for example phosphate buffered saline or citrate buffered saline). In some embodiments, the pharmaceutically carrier comprises an oil (for example corn, sesame, cottonseed, soybean, or safflower oil). The pharmaceutical composition may further include one or more additives including suspending agents, surfactants, dispersing agents, and preservatives (such as an antioxidant).

In some embodiments of the pharmaceutical composition, the compounds of Formula (I), which may be compounds of Formula (II) and/or Formula (III), can be incorporated in a homogeneously dispersed formulation. In some embodiments of the pharmaceutical composition, the compounds of Formula (I), which may be compounds of Formula (II) and/or Formula (III), can be incorporated in an emulsified formulation. In some embodiments of the pharmaceutical composition, the compounds of Formula (I), which may be compounds of Formula (II) and/or Formula (III), can be incorporated in an oil-in-water formulation. An oil-in-water formulation can comprise an oil component, an aqueous component, and one or more surfactants (for example formulations comprising soybean oil, TWEEN 80, SPAN 85, and phosphate buffered saline). In some embodiments of the pharmaceutical composition, the compounds of Formula (I), which may be compounds of Formula (II) and/or Formula (III), can be incorporated into a liposome formulation.

In some embodiments, the pharmaceutical composition can further comprise an antigen in an amount effective to generate an immune response against the antigen. In some embodiments, the antigen is a vaccine.

The pharmaceutical composition can be administered in any suitable manner (parenterally or non-parenterally). In some embodiments, the pharmaceutical composition can be administered by an intradermal, subcutaneous, intramuscular, or intravenous injection.

In any embodiment of a pharmaceutical composition comprising a compound of Formula (II), the compound of Formula (II) is present in the composition in at least 80% enantiomeric excess, relative to the compound of Formula (I), at least 90% enantiomeric excess, at least 95% enantiomeric excess, at least 96% enantiomeric excess, at least 96% enantiomeric excess, at least 97% enantiomeric excess, at least 98% enantiomeric excess, at least 99% enantiomeric excess, at least 99.5% enantiomeric, or at least 99.8% enantiomeric excess.

In any embodiment of a pharmaceutical composition comprising a compound of Formula (II), the opposite enantiomer to the compound of Formula (III) is present in the composition in less than 10%, less than 5%, less than 2.5%, less than 2%, less than 1.5%, less than 1%, less than 0.5%, less than 0.25%, or less than 0.1%.

The exact amount of compound or salt used in a pharmaceutical composition of the disclosure will vary according to factors known to those of skill in the art, such as the physical and chemical nature of the compound or salt, the nature of the carrier, and the intended dosing regimen.

In some embodiments, the concentration of a compound of Formula (I), which may be a compound of Formula (II) and/or Formula (III), in the pharmaceutical composition can be at least 0.0005 mg/mL, at least 0.001 mg/mL, or at least 0.05 mg/mL. In some embodiments, the concentration of a compound of Formula (I), which may be a compound of Formula (II) and/or Formula (III), in the pharmaceutical composition can be up to 2.4 mg/mL, up to 0.06 mg/mL, up to 0.01 mg/mL, or up to 0.005 mg/mL.

In some embodiments, the compositions of the disclosure will contain sufficient active ingredient or prodrug to provide a dose of at least 100 nanograms per kilogram (ng/kg), or at least 10 micrograms per kilogram (μg/kg), of the compound or salt to the subject. In some embodiments, the compositions of the disclosure will contain sufficient active ingredient or prodrug to provide a dose of up to 50 milligrams per kilogram (mg/kg), or up to 5 mg/kg, of the compound or salt to the subject.

In some embodiments, the compositions of the disclosure will contain sufficient active ingredient or prodrug to provide a dose of, for example, from 0.01 mg/m$^2$ to 5.0 mg/m$^2$, computed according to the Dubois method, in which the body surface area of a subject (m$^2$) is computed using the subject's body weight: m$^2$=(wt kg$^{0.425}$×height cm$^{0.725}$)× 0.007184, although in some embodiments the methods may be performed by administering a compound or salt or composition in a dose outside this range. In some of these embodiments, the method includes administering sufficient compound to provide a dose of from 0.1 mg/m$^2$ to 2.0 mg/m$^2$ to the subject, for example, a dose of from 0.4 mg/m$^2$ to 1.2 mg/m$^2$.

A variety of dosage forms may be used to administer the compounds or salts of the disclosure to a human or animal. Dosage forms that can be used include, for example, tablets, lozenges, capsules, parenteral formulations, creams, ointments, topical gels, aerosol formulations, liquid formulations (e.g., aqueous formulation), transdermal patches, and the like. These dosage forms can be prepared with conventional pharmaceutically acceptable carriers and additives using conventional methods, which generally include the step of bringing the active ingredient into association with the carrier. A preferred dosage form has one or more of compounds or salts of the disclosure dissolved in an aqueous formulation.

Compounds or salts disclosed herein induce the production of certain cytokines in experiments performed according to the description of the Examples. These results indicate that the compounds or salts are useful for enhancing the immune response in a number of different ways, making them useful in the treatment of a variety of disorders.

The compounds or salts described herein can be administered as the single therapeutic agent in the treatment regimen, or the compounds or salts described herein may be administered in combination with other active agents, including antivirals, antibiotics, proteins, peptides, oligonucleotides, antibodies, etc.

Compounds or salts described herein induce the production of cytokines (e.g., IFN-alpha, IFN-gamma, TNF-alpha, IP-10) in experiments performed according to the tests set forth below. These results indicate that the compounds of the disclosure or salts are useful for activating the immune response in a number of different ways, rendering them useful in the treatment of a variety of disorders. As such, the compounds or salts of the disclosure (particularly compounds or salts of Formula II) are agonists of cytokine biosynthesis and production, particularly agonists of IFN-alpha, IFN-gamma, TNF-alpha, and IP-10 cytokine biosynthesis and production.

It is believed that one way in which the compounds or salts of the disclosure (particularly compounds or salts of Formula II) induce cytokine production is through the activation of Toll-like receptors (TLRs) in the immune system, particularly TLR-7 and/or TLR-8, however other mechanisms may be involved. It is believed that in the immune system pathways (i.e., mechanisms) for cytokine induction, the compounds or salts of the disclosure (particularly compounds or salts of Formula II) primarily act as agonists of TLR-7 and/or TLR-8, however, other pathways or activities may be involved.

Administration of the compounds or salts described herein can induce the production of interferon-alpha (IFN-alpha), interferon-gamma (IFN-gamma), tumor necrosis factor-alpha (TNF-alpha), and IP-10 in cells. Cytokines whose biosynthesis can be induced by compounds or salts of the disclosure include IFN-alpha, IFN-gamma, TNF-alpha, IP-10, and a variety of other cytokines. Among other effects, these cytokines can inhibit virus production and tumor cell growth, making the compounds or salts useful in the treatment of viral diseases and neoplastic diseases. Accordingly, the disclosure provides a method of inducing cytokine biosynthesis in a human or animal by administering an effective amount of a compound or salt of the disclosure to the human or animal. The human or animal to which the compound or salt is administered for induction of cytokine production may have one or more diseases, disorders, or conditions described below, for example a viral disease or a neoplastic disease, and administration of the compound or salt may provide therapeutic treatment. Alternatively, the compound or salt may be administered to the human or animal prior to the human or animal acquiring the disease so that administration of the compound or salt may provide a prophylactic treatment.

In addition to the ability to induce the production of cytokines, compounds or salts described herein can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. In addition, the compounds or salts may cause proliferation and differentiation of B-lymphocytes.

Conditions for which compounds or salts or compositions identified herein may be used as treatment include, but are not limited to:

Viral diseases such as, for example, diseases resulting from infection by an adenovirus, a herpes virus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenza virus, avian influenza), a paramyxovirus (e.g., parainfluenza virus, mumps virus, measles virus, and respiratory syncytial virus (RSV), a coronavirus (e.g., SARS), a papovavirus (e.g., papillomaviruses, such as those that cause genital warts, common warts, or plantar warts), hepadnavirus (e.g., hepatitis B virus), a flavivirus (e.g., hepatitis C virus or Dengue virus), or a retrovirus (e.g., a lentivirus such as HIV), ebola virus;

Neoplastic diseases such as bladder cancer, cervical dysplasia, cervical cancer, actinic keratosis, basal cell carcinoma, cutaneous T-cell lymphoma, mycosis fungoides, Sezary Syndrome, HPV associated head and neck cancer (e.g., HPV positive oropharyngeal squamous cell carcinoma), Kaposi's sarcoma, melanoma, squamous cell carcinoma, renal cell carcinoma, acute myeloid leukemia, chronic myeloid leukemia, chronic lymphocytic leukemia, multiple myeloma, Hodgkin's lymphoma, non-Hodgkin's lymphoma, B-cell lymphoma, hairy cell leukemia, esophageal cancer, and other cancers;

$T_H2$-mediated atopic diseases such as atopic dermatitis or eczema, eosinophilia, asthma, allergy, allergic rhinitis, and Omenn's syndrome;

Diseases associated with wound repair, such as, for example, inhibition of keloid formation and other types of scarring (e.g., enhancing wound healing, including chronic wounds); and Parasitic diseases including but not limited to malaria, leishmaniasis, cryptosporidiosis, toxoplasmosis, and trypanosome infection.

In addition, a compound, salt, or pharmaceutical composition described herein may be used as a vaccine adjuvant for use in conjunction with any material that increases either humoral and/or cell mediated immune responses, such as, for example, tumor antigens (e.g., MAGE-3, NY-ESO-1); live viral, bacterial, or parasitic immunogens; inactivated viral, protozoal, fungal, or bacterial immunogens; toxoids; toxins; polysaccharides; proteins; glycoproteins; peptides; cellular vaccines; DNA vaccines; autologous vaccines; recombinant proteins; and the like.

Examples of vaccines that can benefit from use of a compound, salt, or composition identified herein as a vaccine adjuvant include BCG vaccine, cholera vaccine, plague vaccine, typhoid vaccine, hepatitis A vaccine, hepatitis B vaccine, hepatitis C vaccine, influenza A vaccine, influenza B vaccine, malaria vaccine, parainfluenza vaccine, polio vaccine, rabies vaccine, measles vaccine, mumps vaccine, rubella vaccine, yellow fever vaccine, tetanus vaccine, diphtheria vaccine, hemophilus influenza b vaccine, tuberculosis vaccine, meningococcal and pneumococcal vaccines, adenovirus vaccine, HIV vaccine, chicken pox vaccine, cytomegalovirus vaccine, dengue vaccine, feline leukemia vaccine, fowl plague vaccine, HSV-1 vaccine and HSV-2 vaccine, hog cholera vaccine, Japanese encephalitis vaccine, respiratory syncytial virus vaccine, rotavirus vaccine, papilloma virus vaccine, yellow fever vaccine, ebola virus vaccine.

Compounds, salts, or pharmaceutical compositions identified herein may be particularly useful as vaccine adjuvants when used in conjunction with tumor antigens associated with colorectal cancer, head and neck cancer, breast cancer, lung cancer and melanoma.

Compounds, salts, or pharmaceutical compositions identified herein may be particularly useful in individuals having compromised immune function. For example, compounds, salts, or compositions may be used for treating opportunistic infections and tumors that occur after suppression of cell mediated immunity in, for example, transplant patients, cancer patients, and HIV patients.

One or more of the above diseases or types of diseases, for example, a viral disease or neoplastic disease may be treated in a human or animal in need thereof (having the disease) by administering a therapeutically effective amount of a compound, salt, or composition to the human or animal.

A human or animal may also be vaccinated by administering an effective amount of a compound, salt, or composition described herein as a vaccine adjuvant. In one embodiment, a method of vaccinating a human or animal includes administering an effective amount of a compound, salt, or composition described herein to the human or animal as a vaccine adjuvant. The vaccine adjuvant can be co-administered with the material that increases one or more humoral and cell mediated immune responses by including each in the same composition. Alternatively, the vaccine adjuvant and the material that increases either humoral and/or cell mediated immune responses can be in separate compositions.

Compounds, salts, or compositions identified herein may as prophylactic or therapeutic vaccine adjuvants in veterinary applications. Compounds, salts, or compositions identified herein may be administered to, for example, pigs, horses, cattle, sheep, dogs, cats, poultry (such as chickens or turkeys), etc.

Compounds or salts or compositions identified herein may be particularly useful when an effective amount is administered to a human or animal to treat bladder cancer, cervical dysplasia, actinic keratosis, basal cell carcinoma, genital warts, herpes virus infection, or cutaneous T-cell lymphoma. For these conditions, administration of the compound, salt, or composition of the disclosure is preferably topical (i.e., applied directly to the surface of a tumor, a lesion, a wart, or an infected tissue, etc.).

In one embodiment an effective amount of compound, salt, or composition described herein, such as an aqueous composition is administered into the bladder of a human or animal that has at least one tumor of the bladder by intravesical instillation (e.g., administration using a catheter).

An amount of a compound or salt effective to induce cytokine biosynthesis will typically cause one or more cell types, such as monocytes, macrophages, dendritic cells, and B-cells to produce an amount of one or more cytokines, such as, for example, IFN-alpha, IFN-gamma, TNF-alpha, and IP-10 that is increased (induced) over a background level of such cytokines. The precise dose will vary according to factors known in the art but is typically to be a dose of 100 ng/kg to 50 mg/kg, or 10 µg/kg to 5 mg/kg. In other embodiments, the amount can be, for example, from 0.01 mg/m$^2$ to 5.0 mg/m$^2$ (computed according to the Dubois method as described above), although in other embodiments the induction of cytokine biosynthesis may be performed by administering a compound or salt in a dose outside this range. In some of these embodiments, the method includes administering sufficient compound or salt or composition to provide a dose from 0.1 mg/m$^2$ to 2.0 mg/m$^2$ to the subject, for example, a dose of from 0.4 mg/m$^2$ to 1.2 mg/m$^2$.

A method of treating a viral infection in a human or animal and a method of treating a neoplastic disease in a human or animal can include administering an effective amount of a compound or salt described herein to the human or animal.

An effective amount to treat or inhibit a viral infection can be an amount that will cause a reduction in one or more of the manifestations of viral infection, such as viral lesions, viral load, rate of virus production, and mortality as compared to untreated humans or animals. The precise amount that is effective for such treatment will vary according to factors known in the art but it is normally a dose of 100 ng/kg to 50 mg/kg, or 10 μg/kg to 5 mg/kg.

An amount of a compound or salt effective to treat a neoplastic condition can be an amount that causes a reduction in tumor size or in the number of tumor foci. The precise amount will vary according to factors known in the art but is typically 100 ng/kg to 50 mg/kg, or 10 μg/kg to 5 mg/kg. In other embodiments, the amount is typically, for example, from 0.01 mg/m² to 5.0 mg/m² (computed according to the Dubois method as described above), although in some embodiments the induction of cytokine biosynthesis may be performed by administering a compound or salt in a dose outside this range. In some of these embodiments, the method includes administering sufficient compound or salt or composition to provide a dose from 0.1 mg/m² to 2.0 mg/m² to the subject, for example, a dose of from 0.4 mg/m² to 1.2 mg/m².

EMBODIMENTS

Embodiment 1 is a compound of Formula (I), or salt thereof:

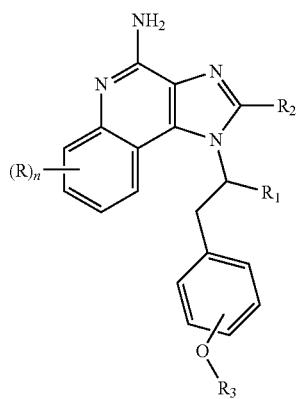

Formula (I)

wherein:

n is an integer of 0 or 1;

R is selected from the group consisting of halogen, hydroxy, alkyl, alkoxy, and —C(O)—O-alkyl;

$R_1$ is —$C_{1-3}$ alkylene-O—$C_{1-3}$ alkyl;

$R_2$ is selected from the group consisting of hydrogen, methyl, ethyl, n-propyl, n-butyl, —CH$_2$OCH$_3$, —CH$_2$OCH$_2$CH$_3$, and —CH$_2$CH$_2$OCH$_3$; and $R_3$ is alkyl, aralkyl, wherein the alkyl or alkyl portion of the aralkyl can be optionally interrupted by one or more non-peroxidic —O— atoms, and wherein the aryl portion of the aralkyl can be optionally substituted with halogen, hydroxy, alkyl, alkoxy, or combinations thereof.

Embodiment 2 is the compound or salt of embodiment 1, which is a compound of Formula (II), or salt thereof:

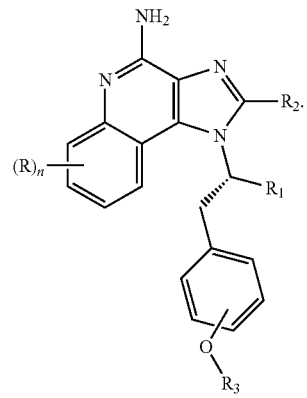

Formula (II)

Embodiment 3 is the compound or salt of embodiment 1, which is a compound of Formula (III), or salt thereof:

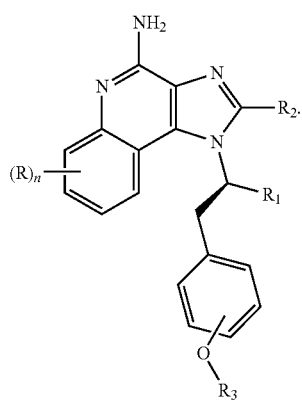

Formula (III)

Embodiment 4 is the compound or salt of any one of embodiments 1 through 3, wherein the —O—$R_3$ group is in a meta or para position.

Embodiment 5 is the compound or salt of embodiment 4, wherein the —O—$R_3$ group is in the para position.

Embodiment 6 is the compound or salt of any of embodiments 1 through 5, wherein R is selected from the group consisting of halogen, hydroxy, —$C_{1-7}$ alkoxy, and —C(O)—O—$C_{1-5}$alkyl.

Embodiment 7 is the compound or salt of embodiment 6, wherein R is selected from the group consisting of hydroxy, F, and Cl.

Embodiment 8 is the compound or salt of embodiment 7, wherein R is selected from the group consisting of F and Cl.

Embodiment 9 is the compound or salt of any one of embodiments 1 through 5, wherein n is 0.

Embodiment 10 is the compound or salt of any one of the embodiments 1 through 9, wherein $R_1$ is —CH$_2$OCH$_3$ or —CH$_2$OCH$_2$CH$_3$.

Embodiment 11 is the compound or salt of embodiment 10, wherein $R_1$ is —CH$_2$OCH$_2$CH$_3$.

Embodiment 12 is the compound or salt of any one of the embodiments 1 through 11, wherein $R_2$ is selected from the group consisting of hydrogen, methyl, and ethyl.

Embodiment 13 is the compound or salt of embodiment 12, wherein $R_2$ is hydrogen or methyl.

Embodiment 14 is the compound or salt of any one of embodiments 1 through 13, wherein $R_3$ has at least 4, at least 5, or at least 6 carbon atoms.

Embodiment 15 is the compound or salt of any one of embodiments 1 through 14, wherein $R_3$ has up to 18, up to 16, or up to 14 carbon atoms.

Embodiment 16 is the compound or salt of embodiment 15, wherein $R_3$ has up to 12 carbon atoms.

Embodiment 17 is the compound or salt of any one of the embodiments 1 through 16, wherein $R_3$ is an alkyl.

Embodiment 18 is the compound or salt of any one of the embodiments 1 through 17, wherein $R_3$ is an alkyl not interrupted by —O— atoms.

Embodiment 19 is the compound or salt of embodiment 17 or 18, wherein $R_3$ is a linear alkyl.

Embodiment 20 is the compound or salt of embodiment 13, wherein $R_3$ is selected from the group consisting of —$(CH_2)_3CH_3$, —$(CH_2)_4CH_3$, —$(CH_2)_5CH_3$, —$(CH_2)_6CH_3$, —$(CH_2)_7CH_3$, and —$(CH_2)_{11}CH_3$.

Embodiment 21 is the compound or salt of embodiment 20, wherein $R_3$ is selected from the group consisting of —$(CH_2)_3CH_3$, —$(CH_2)_5CH_3$, —$(CH_2)_7CH_3$, and —$(CH_2)_{11}CH_3$.

Embodiment 22 is the compound or salt of embodiment 21, wherein $R_3$ is —$(CH_2)_3CH_3$.

Embodiment 23 is the compound or salt of embodiment 21, wherein $R_3$ is —$(CH_2)_5CH_3$.

Embodiment 24 is the compound or salt of embodiment 21, wherein $R_3$ is —$(CH_2)_7CH_3$.

Embodiment 25 is the compound or salt of embodiment 21, wherein $R_3$ is —$(CH_2)_{11}CH_3$.

Embodiment 26 is the compound or salt of embodiment 17 or 18, wherein $R_3$ is a branched alkyl.

Embodiment 27 is the compound or salt of embodiment 26, wherein $R_3$ is —$CH_2$—$CH(CH_2CH_3)$—$(CH_2)_3CH_3$.

Embodiment 28 is the compound or salt of any one of the embodiments 1 through 16, wherein $R_3$ is an aralkyl.

Embodiment 29 is the compound or salt of embodiment 28, wherein $R_3$ is an aralkyl having an alkyl not interrupted by —O— atoms.

Embodiment 30 is the compound or salt of embodiment 29, wherein $R_3$ is —$CH_2$-phenyl.

Embodiment 31 is the compound or salt of any one of embodiments 1 through 30, wherein $R_1$ is —$C_{1-3}$ alkylene-O—$C_{1-3}$ alkyl; $R_2$ is selected from the group consisting of hydrogen, methyl, and ethyl; $R_3$ is —$C_{4-12}$ alkyl; and n is 0.

Embodiment 32 is the compound or salt of embodiment 31, wherein $R_1$ is —$CH_2OCH_3$ or —$CH_2OCH_2CH_3$; $R_2$ is selected from the group consisting of hydrogen, methyl, and ethyl; $R_3$ is —$C_{4-12}$alkyl; and n is 0.

Embodiment 33 is the compound or salt of embodiment 32, wherein $R_2$ is hydrogen.

Embodiment 34 is the compound or salt of embodiment 32 or 33, wherein $R_3$ is selected from the group consisting of —$(CH_2)_3CH_3$, —$(CH_2)_4CH_3$, —$(CH_2)_5CH_3$, —$(CH_2)_6CH_3$, —$(CH_2)_7CH_3$, and —$(CH_2)_{11}CH_3$.

Embodiment 35 is the compound or salt of embodiment 34, wherein $R_3$ is selected from the group consisting of —$(CH_2)_3CH_3$, —$(CH_2)_5CH_3$, —$(CH_2)_7CH_3$, and —$(CH_2)_{11}CH_3$.

Embodiment 36 is the compound or salt of embodiment 35, wherein $R_3$ is —$(CH_2)_3CH_3$.

Embodiment 37 is the compound or salt of embodiment 36, wherein the compound is 1-[(1S)-1-[(4-butoxyphenyl)methyl]-2-ethoxy-ethyl]imidazo[4,5-c]quinolin-4-amine.

Embodiment 38 is the compound or salt of embodiment 35, wherein $R_3$ is —$(CH_2)_5CH_3$.

Embodiment 39 is the compound or salt of embodiment 36, wherein the compound is 1-[(1S)-1-(ethoxymethyl)-2-(4-hexoxyphenyl)ethyl]imidazo[4,5-c]quinolin-4-amine.

Embodiment 40 is the compound or salt of embodiment 35, wherein $R_3$ is —$(CH_2)_7CH_3$.

Embodiment 41 is the compound or salt of embodiment 40, wherein the compound is 1-[(1S)-1-(ethoxymethyl)-2-(4-octoxyphenyl)ethyl]imidazo[4,5-c]quinolin-4-amine.

Embodiment 42 is the compound or salt of embodiment 35, wherein $R_3$ is —$(CH_2)11CH_3$.

Embodiment 43 is the compound or salt of embodiment 42, wherein the compound is 1-[(1S)-1-[(4-dodecoxyphenyl)methyl]-2-ethoxy-ethyl]imidazo[4,5-c]quinolin-4-amine.

Embodiment 44 is the compound or salt of any one of the embodiments 1 through 43, wherein the pharmaceutically acceptable salt is hydrochloride.

Embodiment 45 is a pharmaceutical composition comprising an effective amount of a compound or salt of any one of the embodiments 1 through 44 in combination with a pharmaceutically acceptable carrier.

Embodiment 46 is the pharmaceutical composition of embodiment 45, wherein the compound of Formula (II) or salt thereof is present in at least 80% enantiomeric excess.

Embodiment 47 is the pharmaceutical composition of embodiment 46, wherein the compound of Formula (II) or salt thereof is present in at least 90% enantiomeric excess.

Embodiment 48 is the pharmaceutical composition of embodiment 47, wherein the compound of Formula (II) or salt thereof is present in at least 95% enantiomeric excess.

Embodiment 49 is the pharmaceutical composition of embodiment 48, wherein the compound of Formula (II) or salt thereof is present in at least 97% enantiomeric excess.

Embodiment 50 is the pharmaceutical composition of embodiment 49, wherein the compound of Formula (II) or salt thereof is present in at least 98% enantiomeric excess.

Embodiment 51 is the pharmaceutical composition of embodiment 50, wherein the compound of Formula (II) or salt thereof is present in at least 99% enantiomeric excess.

Embodiment 52 is the pharmaceutical composition of embodiment 51, wherein the compound of Formula (II) or salt thereof is present in at least 99.5% enantiomeric excess.

Embodiment 53 is the pharmaceutical composition of embodiment 52, wherein the compound of Formula (II) or salt thereof is present in at least 99.8% enantiomeric excess.

Embodiment 54 is the pharmaceutical composition of any one of the embodiments 45 through 53, further comprising an antigen.

Embodiment 55 is the pharmaceutical composition of any one of the embodiments 45 through 54 for use in treating an infectious disease in a human or animal.

Embodiment 56 is the pharmaceutical composition of embodiment 55 for use in treating a viral, bacterial, fungal, or parasitic infection in a human or animal.

Embodiment 57 is a method of inducing cytokine biosynthesis in a human or animal comprising administering an effective amount of a compound or salt of any one of the embodiments 1 through 44 to the human or animal.

Embodiment 58 is a method of embodiment 57 comprising administering an effective amount of a compound or salt of any one of the embodiments 2 and 4 through 44 as dependent on embodiment 2 to the human or animal.

Embodiment 59 is a method of inducing biosynthesis of IFN-alpha in a human or animal comprising administering an effective amount of a compound or salt of any one of the embodiments 1 through 44 to the human or animal.

Embodiment 60 is a method of embodiment 59 comprising administering an effective amount of a compound or salt of any one of the embodiments 2 and 4 through 44 as dependent on embodiment 2 to the human or animal.

Embodiment 61 is a method of inducing biosynthesis of IFN-gamma in a human or animal comprising administering an effective amount of a compound or salt of any one of the embodiments 1 through 44 to the human or animal.

Embodiment 62 is a method of embodiment 61 comprising administering an effective amount of a compound or salt of any one of the embodiments 2 and 4 through 44 as dependent on embodiment 2 to the human or animal.

Embodiment 63 is a method of inducing biosynthesis of TNF-alpha in a human or animal comprising administering an effective amount of a compound or salt of any one of the embodiments 1 through 44 to the human or animal.

Embodiment 64 is a method of embodiment 63 comprising administering an effective amount of a compound or salt of any one of the embodiments 2 and 4 through 44 as dependent on embodiment 2 to the human or animal.

Embodiment 65 is a method of inducing biosynthesis of IP-10 in a human or animal comprising administering an effective amount of a compound or salt of any one of the embodiments 1 through 44 to the human or animal.

Embodiment 66 is a method of embodiment 65 comprising administering an effective amount of a compound or salt of any one of the embodiments 2 and 4 through 44 as dependent on embodiment 2 to the human or animal.

Embodiment 67 is a compound or salt of any one of the embodiments 1 through 44 for use as a vaccine adjuvant in treating an infectious disease in a human or animal.

Embodiment 68 is a compound or salt of any one of the embodiments 2 and 4 through 44 as dependent on embodiment 2 for use as a vaccine adjuvant in treating an infectious disease in a human or animal.

Embodiment 69 is a compound or salt of any one of the embodiments 1 through 44 for use as a vaccine adjuvant in treating a viral, bacterial, fungal, or parasitic infection in a human or animal.

Embodiment 70 is a compound or salt of any one of the embodiments 2 and 4 through 44 as dependent on embodiment 2 for use as a vaccine adjuvant in treating a viral, bacterial, fungal, or parasitic infection in a human or animal.

Embodiment 71 is a compound or salt of any one of embodiments 67 through 70, wherein the treatment is a therapeutic or prophylactic treatment.

EXAMPLES

Objects and advantages of the disclosure are further illustrated by the examples provided herein. The particular materials and amounts thereof recited in these examples, as well as other conditions and details, are merely illustrative and are not intended to be limiting. The person of ordinary skill in the art, after carefully reviewing the entirety of this disclosure, will be able to use materials and conditions in addition to those specifically described in the examples.

Column chromatography purification of compounds was conducted using an ISOLARA HPFC system (an automated high-performance flash chromatography purification instrument available from Biotage, Inc, Charlottesville, Va.). The eluent used for each purification is described in the examples.

Proton nuclear magnetic resonance ($^1$H NMR) analysis was conducted using a BRUKER A500 NMR spectrometer (Bruker Corporation, Billerica, Mass.).

Sodium borohydride ($NaBH_4$), 10% palladium on carbon, cesium carbonate ($Cs_2CO_3$), 1-iodooctane, 1-bromohexane, 2-ethylhexyl iodide, and N-methylmorpholine were obtained from the Sigma-Aldrich Company, St. Louis, Mo.

Diethyl sulfate, triethyl orthoformate, 3% platinum on carbon, benzyl bromide, 1-bromobutane, n-propyl acetate, para-toluenesulfonyl chloride, and pyridine hydrochloride were obtained from the Alfa Aesar Company, Haverhill, Mass.

(2S)-2-(tert-butoxycarbonylamino)-3-(4-tert-butoxyphenyl)propanoic acid (CAS Number 47375-34-8), isobutyl chloroformate, tetrabutylammonium chloride, and 3-chloroperbenzoic acid (about 80% MCPBA, which was determined iodometrically according to Braun, G. Org. Synth., Collective Volume 1932, 1, 431) were obtained from Oakwood Products Incorporated, Estill, S.C.

1-Bromododecane was obtained from Avocado Research Chemicals, Heysham, UK.

Example 1

1-[(1 S)-1-[(4-dodecoxyphenyl)methyl]-2-ethoxyethyl]imidazo[4,5-c]quinolin-4-amine

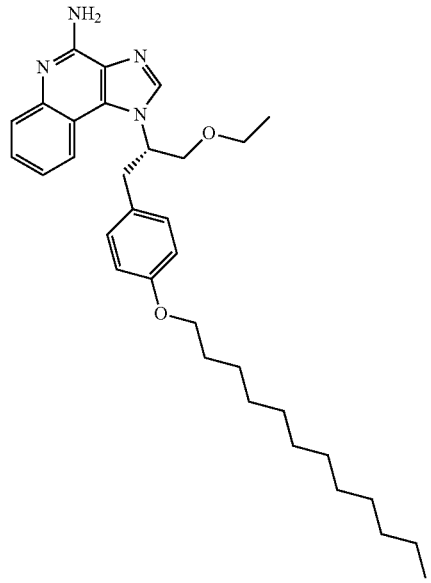 [SMILES: CCCCCCCCCCCCOc1ccc(C[C@@H](COCC)n2cnc3c(N)nc4ccccc4c32)cc1]

Part A

A stirred solution (2S)-2-(tert-butoxycarbonylamino)-3-(4-tert-butoxyphenyl)propanoic acid (5.00 g, 14.8 mmol) in 15 mL of anhydrous tetrahydrofuran (THF) was cooled to −15° C. in an ice/methanol bath. The chilled solution was combined with N-methylmorpholine (1.63 mL, 14.8 mmol) followed by the addition of isobutyl chloroformate (1.92 mL, 14.8 mmol). After stirring for 5 minutes, the reaction mixture was filtered and rinsed with small portions of THF to remove N-methylmorpholine hydrochloride. The resulting filtrate was returned to the cold bath and a solution of 1.12 g of $NaBH_4$ in 7 mL of water was carefully added. After stirring for 20 minutes, the reaction mixture was combined with 75 mL of water followed by the addition of 100 mL of ethyl acetate. The layers were separated and the aqueous layer was extracted with an additional 25 mL of ethyl acetate. The combined organic portions were washed with water and brine, dried over $Na_2SO_4$, filtered, and concentrated to give a colorless syrup. The syrup was concentrated from heptanes to give 4.56 g of tert-butyl N-[(1S)-1-[(4-tert-butoxyphenyl)methyl]-2-hydroxy-ethyl]carbamate as a white solid.

Part B

A stirred solution of tert-butyl N-[(1S)-1-[(4-tert-butoxyphenyl)methyl]-2-hydroxy-ethyl]carbamate (4.56 g, 14.1 mmol) in 40 mL of heptane was heated to 35° C. and combined with 2.8 g of 50% NaOH solution and diethyl sulfate (2.31 mL, 17.6 mmol). The reaction mixture was then combined with 390 mg of tetrabutylammonium chloride hydrate. After stirring for 2 hours, the reaction mixture was quenched with 15 mL of saturated $NH_4OH$ solution. After stirring for 1 hour, water was added to the reaction and the layers were separated. The aqueous layer was extracted with an additional 20 mL of heptane. The combined organic portions were washed successively with water and brine, dried over $Na_2SO_4$, filtered, and concentrated under reduced pressure to give 4.17 g of tert-butyl N-[(1S)-1-[(4-tert-butoxyphenyl)methyl]-2-ethoxy-ethyl]carbamate as a colorless oil.

Part C

Concentrated hydrochloric acid (4 mL) was added to a solution of tert-butyl N-[(1S)-1-[(4-tert-butoxyphenyl)methyl]-2-ethoxy-ethyl]carbamate (4.17 g, 11.9 mmol) in 30 mL of ethanol and the resulting mixture was heated to reflux for 2 hours. The reaction was then concentrated under reduced pressure to give a colorless syrup. The syrup was again concentrated from ethanol and the resulting syrup was dissolved in 15 mL of hot acetonitrile. Crystals formed and were isolated by filtration. The filtrate was concentrated and a second crop of crystals was obtained from acetonitrile. The combined crops yielded 2.09 g of 4-[(2S)-2-amino-3-ethoxy-propyl]phenol hydrochloride as a white solid.

Part D

A suspension of 4-[(2S)-2-amino-3-ethoxy-propyl]phenol hydrochloride (2.09 g, 9.59 mmol) in 40 mL of dichloromethane was combined with triethylamine (4.00 milliliters, 28.8 mmol) followed by the addition of 4-chloro-3-nitroquinoline (1.99 g, 9.59 mmoL) and the reaction mixture was stirred under an atmosphere of nitrogen overnight. The reaction mixture was concentrated to give a yellow solid. The solid was dissolved in 75 mL of warm ethyl acetate and washed with water (2×) and brine. The organic portion was dried over $Na_2SO_4$, filtered and concentrated to give 3.23 g of 4-[(2S)-3-ethoxy-2-[(3-nitro-4-quinolyl)amino]propyl]phenol as a yellow solid.

Part E

A suspension of 4-[(2S)-3-ethoxy-2-[(3-nitro-4-quinolyl)amino]propyl]phenol (3.23 g, 8.08 mmol) in 150 mL of a 1:1 mixture of acetonitrile/toluene was placed in a pressure bottle and 300 mg of 3% platinum on carbon was added. The bottle was then shaken under an atmosphere of hydrogen (40 PSI) for 18 hours. The reaction mixture was filtered through a pad of CELITE, rinsing with acetonitrile. The filtrate was concentrated under reduced pressure to give 2.96 g of 4-[(2S)-2-[(3-amino-4-quinolyl)amino]-3-ethoxy-propyl]phenol as a yellow foam.

Part F

A solution of 4-[(2S)-2-[(3-amino-4-quinolyl)amino]-3-ethoxy-propyl]phenol (2.96 g, 8.78 mmol) in 50 mL of n-propyl acetate was combined with triethyl orthoformate (2.91 mL, 17.6 mmol) and 300 mg of pyridine hydrochloride and the mixture was heated to 100° C. overnight. An additional 3 mL of triethyl orthoformate was added to the reaction mixture and heating was continued for 5 hours. The cooled reaction mixture was diluted with 50 mL of ethyl acetate and washed successively with saturated $NaHCO_3$ solution, water and brine. The organic portion was dried over $Na_2SO_4$, filtered, and concentrated to give a light brown syrup. Purification by column chromatography ($SiO_2$, 1% methanol/chloroform to 7.5% methanol/chloroform) gave 2.20 g of 4-[(2S)-3-ethoxy-2-imidazo[4,5-c]quinolin-1-yl-propyl]phenol as an off-white foam.

Part G

To a stirred solution of 4-[(2S)-3-ethoxy-2-imidazo[4,5-c]quinolin-1-yl-propyl]phenol (695 mg, 2.00 mmol) in 10 mL of anhydrous N,N-dimethylformamide (DMF), $Cs_2CO_3$ (977 mg, 3.00 mmol) was added followed by the addition of 1-bromododecane (496 microliters, 2.16 mmol). The reaction mixture was heated to 65° C. under an atmosphere of nitrogen. After 4 hours, the reaction mixture was concentrated under reduced pressure and the resulting syrup was dissolved in 50 mL of ethyl acetate and washed successively with water (2×) and brine. The organic portion was dried over $Na_2SO_4$, filtered, and concentrated. Purification by column chromatography ($SiO_2$, 1% methanol/chloroform to 5% methanol/chloroform) gave 713 mg of 1-[(1S)-1-[(4-dodecoxyphenyl)methyl]-2-ethoxy-ethyl]imidazo[4,5-c]quinoline as an amber syrup.

Part H

A solution of 1-[(1S)-1-[(4-dodecoxyphenyl)methyl]-2-ethoxy-ethyl]imidazo[4,5-c]quinoline (713 mg, 1.38 mmol) in 20 mL of dichloromethane was combined with 297 mg of MCPBA and stirred for 50 minutes. A 10% solution of $Na_2CO_3$ in water (10 mL) was then added and the mixture was diluted with an additional 20 mL of dichloromethane. The layers were separated. The organic portion was washed successively with water and brine, dried over $Na_2SO_4$, filtered, and concentrated under reduced pressure. The resulting material was dissolved in 20 mL of dichloromethane and combined with 7 mL of concentrated $NH_4OH$ solution and para-toluenesulfonyl chloride (289 mg, 1.52 mmol). After stirring rapidly for 45 minutes, the reaction mixture was diluted with 10 mL of dichloromethane and washed successively with water (3×) and brine. The organic portion was dried over $Na_2SO_4$, filtered, and concentrated under reduced pressure. Purification by column chromatography ($SiO_2$, 1% methanol/chloroform to 10% methanol/chloroform) gave 536 mg of an amber foam. The foam was dissolved in 10 mL of ethanol, combined with 0.25 mL of concentrated hydrochloric acid, and then concentrated under reduced pressure. The resulting syrup was concentrated from acetonitrile to provide a solid. The solid was isolated by filtration, rinsed with cold acetonitrile, and dried with suction to give 279 mg of 1-[(1S)-1-[(4-dodecoxyphenyl)methyl]-2-ethoxy-ethyl]imidazo[4,5-c]quinolin-4-amine as the hydrochloride salt (white powder). $^1$H NMR ($CD_3OD$, 500 MHz) δ 8.62 (s, 1H), 8.36 (d, J=8.4 Hz, 1H), 7.75-7.69 (m, 2H), 7.57 (t, J=7.6 Hz, 1H), 7.02 (d, J=8.6 Hz, 2H), 6.66 (m, 2H), 5.65 (m, 1H), 4.03 (d, J=5.1, 1H), 3.81 (t, J=6.4 Hz, 1H), 3.55 (m, 2H), 3.43 (dd, J=5.8, 14.3 Hz, 1H), 3.33 (m, 1H), 1.69 (m, 2H), 1.41 (m, 2H), 1.36-1.26 (m, 16H), 1.13 (t, J=7.0 Hz, 3H), 0.92 (t, J=7.0 Hz, 3H).

Example 2

1-[(1S)-1-(ethoxymethyl)-2-(4-octoxyphenyl)ethyl]imidazo[4,5-c]quinolin-4-amine

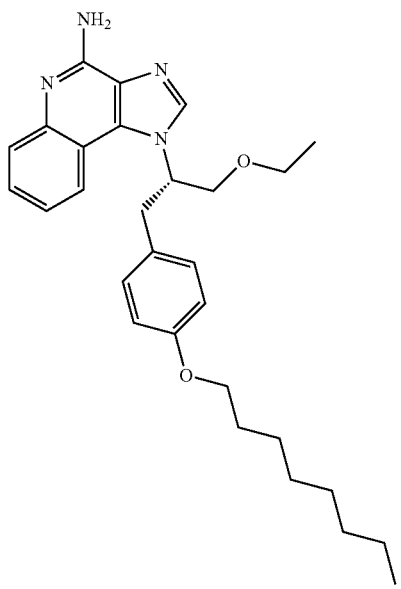 [SMILES: CCCCCCCCOc1ccc(C[C@@H](COCC)n2cnc3c(N)nc4ccccc4c32)cc1]

Part A

To a stirred solution of 4-[(2S)-3-ethoxy-2-imidazo[4,5-c]quinolin-1-yl-propyl]phenol (695 mg, 2.00 mmol) in 10 mL of anhydrous DMF, $Cs_2CO_3$ (977 mg, 3.00 mmol) was added followed by the addition of 1-iodooctane (397 microliters, 2.20 mmol). The reaction mixture was heated to 65° C. under an atmosphere of nitrogen. After 4 hours, the reaction mixture was concentrated under reduced pressure. The resulting syrup was dissolved in 50 mL of ethyl acetate and washed successively with water (3×) and brine. The organic portion was dried over $Na_2SO_4$, filtered, and concentrated. Purification by column chromatography ($SiO_2$, 1% methanol/chloroform to 5% methanol/chloroform) gave 709 mg of 1-[(1S)-1-(ethoxymethyl)-2-(4-octoxyphenyl)ethyl]imidazo[4,5-c]quinoline as an amber syrup.

Part B

A solution of 1-[(1S)-1-(ethoxymethyl)-2-(4-octoxyphenyl)ethyl]imidazo[4,5-c]quinoline (709 mg, 1.54 mmol) in 20 mL of dichloromethane was combined with 332 mg of MCPBA and stirred for 50 minutes. A 10% solution of $Na_2CO_3$ in water (10 mL) was then added and the mixture was diluted with an additional 20 mL of dichloromethane. The layers were separated. The organic portion was washed successively with water and brine, dried over $Na_2SO_4$, filtered, and concentrated under reduced pressure. The resulting material was dissolved in 20 mL of dichloromethane and combined with 7 mL of concentrated $NH_4OH$ solution and para-toluenesulfonyl chloride (322 mg, 1.69 mmol). After stirring rapidly for 1 hour, the reaction mixture was diluted with 10 mL of dichloromethane and washed successively with water (3×) and brine. The organic portion was dried over $Na_2SO_4$, filtered, and concentrated under reduced pressure. Purification by column chromatography ($SiO_2$, 1% methanol/chloroform to 10% methanol/chloroform) gave 560 mg of an amber syrup. The syrup was dissolved in 10 mL of ethanol, combined with 0.25 mL of concentrated hydrochloric acid, and then concentrated under reduced pressure. The resulting syrup was then concentrated from acetonitrile to give a solid. The solid was isolated by filtration, rinsed with cold acetonitrile and dried with suction to give 390 mg of 1-[(1S)-1-(ethoxymethyl)-2-(4-octoxyphenyl)ethyl]imidazo[4,5-c]quinolin-4-amine as the hydrochloride salt (white powder). $^1$H NMR ($CD_3OD$, 500 MHz) δ 8.62 (s, 1H), 8.36 (d, J=8.3 Hz, 1H), 7.77-7.68 (m, 2H), 7.56 (t, J=7.6 Hz, 1H), 7.02 (d, J=8.5 Hz, 2H), 6.66 (m, 2H), 5.65 (m, 1H), 4.02 (d, J=5.1, 1H), 3.79 (t, J=6.4 Hz, 1H), 3.55 (m, 2H), 3.43 (dd, J=5.8, 14.3 Hz, 1H), 3.32 (dd, J=9.2, 14.0 Hz, 1H), 1.66 (m, 2H), 1.39 (m, 2H), 1.35-1.26 (m, 8H), 1.13 (t, J=7.0 Hz, 3H), 0.91 (t, J=6.8 Hz, 3H).

Example 3

1-[(1S)-1-[(4-butoxyphenyl)methyl]-2-ethoxy-ethyl]imidazo[4,5-c]quinolin-4-amine

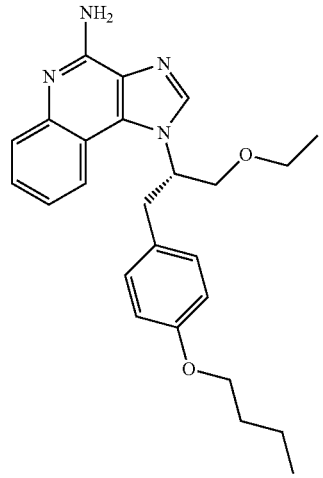 [SMILES: CCCCOc1ccc(C[C@@H](COCC)n2cnc3c(N)nc4ccccc4c32)cc1]

Part A

To a stirred solution of 4-[(2S)-3-ethoxy-2-imidazo[4,5-c]quinolin-1-yl-propyl]phenol (791 mg, 2.27 mmol) in 5 mL of anhydrous DMF, $Cs_2CO_3$ (1.11 g, 3.40 mmol) was added followed by the addition of 1-bromobutane (270 microliters, 2.50 mmol). The reaction mixture was heated to 65° C. under an atmosphere of nitrogen. After stirring overnight, the reaction mixture was concentrated under reduced pressure. The resulting syrup was dissolved in 50 mL of ethyl acetate and washed successively with water (3×) and brine. The organic portion was dried over $Na_2SO_4$, filtered, and concentrated. Purification by column chromatography ($SiO_2$, 1% methanol/chloroform to 5% methanol/chloroform) gave 644 mg of 1-[(1S)-1-(ethoxymethyl)-2-(4-butoxyphenyl)ethyl]imidazo[4,5-c]quinoline as an amber syrup.

Part B

A solution of 1-[(1S)-1-(ethoxymethyl)-2-(4-butoxyphenyl)ethyl]imidazo[4,5-c]quinoline (644 mg, 1.59 mmol) in 25 mL of dichloromethane was combined with 344 mg of MCPBA and stirred for 50 minutes. A 10% solution of $Na_2CO_3$ in water (10 mL) was then added and the mixture was diluted with an additional 20 mL of dichloromethane. The layers were separated. The organic portion was washed successively with water and brine, and then concentrated under reduced pressure. The resulting material was dissolved in 20 mL of dichloromethane and combined with 7 mL of concentrated NH₄OH solution and para-toluenesulfonyl chloride (333 mg, 1.75 mmol). After stirring rapidly for 1 hour, the reaction mixture was diluted with 20 mL of dichloromethane and washed successively with water (3×) and brine. The organic portion was dried over $Na_2SO_4$, filtered, and concentrated under reduced pressure. Purification by column chromatography ($SiO_2$, 1% methanol/chloroform to 10% methanol/chloroform) gave 560 mg of an amber syrup. The syrup was dissolved in 10 mL of ethanol, combined with 0.25 mL of concentrated hydrochloric acid, and then concentrated under reduced pressure. The resulting syrup was crystallized from acetonitrile. The crystals were isolated by filtration, rinsed with cold acetonitrile and dried with suction to give 301 mg of 1-[(1S)-1-[(4-butoxyphenyl)methyl]-2-ethoxy-ethyl]imidazo[4,5-c]quinolin-4-amine as the hydrochloride salt (cream-colored powder). ¹H NMR (CD₃OD, 500 MHz) δ 8.62 (s, 1H), 8.35 (d, J=8.3 Hz, 1H), 7.77-7.68 (m, 2H), 7.56 (t, J=7.6 Hz, 1H), 7.02 (d, J=8.5 Hz, 2H), 6.66 (m, 2H), 5.65 (m, 1H), 4.04 (d, J=5.1, 1H), 3.80 (t, J=6.4 Hz, 1H), 3.56 (m, 2H), 3.43 (dd, J=5.8, 14.3 Hz, 1H), 3.32 (dd, J=9.2, 13.6 Hz, 1H), 1.65 (m, 2H), 1.43 (m, 2H), 1.13 (t, J=7.0 Hz, 3H), 0.95 (t, J=7.4 Hz, 3H).

Example 4

1-[(1S)-1-(ethoxymethyl)-2-(4-hexoxyphenyl)ethyl]imidazo[4,5-c]quinolin-4-amine

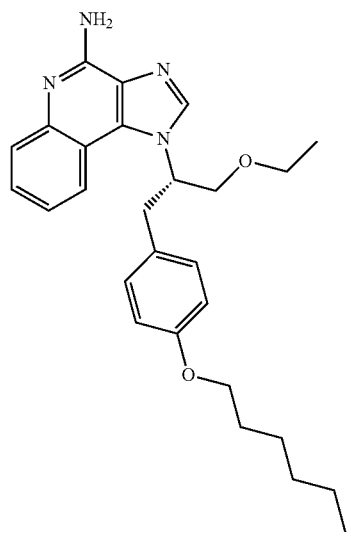 [SMILES: CCCCCCOc1ccc(C[C@@H](COCC)n2cnc3c(N)nc4ccccc4c32)cc1]

Part A

To a stirred solution of 4-[(2S)-3-ethoxy-2-imidazo[4,5-c]quinolin-1-yl-propyl]phenol (495 mg, 1.43 mmol) dissolved in 4 mL of anhydrous DMF, $Cs_2CO_3$ (699 mg, 2.15 mmol) was added followed by the addition of 1-bromohexane (219 microliters, 1.57 mmol). The reaction mixture was heated to 65° C. under an atmosphere of nitrogen. After stirring overnight, the reaction mixture was concentrated under reduced pressure. The resulting syrup was dissolved in 50 mL of ethyl acetate and washed successively with water (3×) and brine. The organic portion was dried over $Na_2SO_4$, filtered, and concentrated. Purification by column chromatography ($SiO_2$, 1% methanol/chloroform to 5% methanol/chloroform) gave 330 mg of 1-[(1S)-1-(ethoxymethyl)-2-(4-hexoxyphenyl)ethyl]imidazo[4,5-c]quinoline as an amber syrup.

Part B

A solution of 1-[(1 S)-1-(ethoxymethyl)-2-(4-hexoxyphenyl)ethyl]imidazo[4,5-c]quinoline (330 mg, 0.77 mmol) in 25 mL of dichloromethane was combined with 165 mg of MCPBA and stirred for 50 minutes. A 10% solution of $Na_2CO_3$ in water (10 mL) was then added and the mixture was diluted with an additional 20 mL of dichloromethane. The layers were separated. The organic portion was washed successively with water and brine, and then concentrated under reduced pressure. The resulting material was dissolved in 20 mL of dichloromethane followed by the addition of 7 mL of concentrated NH₄OH solution and para-toluenesulfonyl chloride (161 mg, 0.85 mmol). After stirring rapidly for 1 hour, the reaction mixture was diluted with 20 mL of dichloromethane and washed successively with water (3×) and brine. The organic portion was dried over $Na_2SO_4$, filtered, and concentrated under reduced pressure. Purification by column chromatography ($SiO_2$, 1% methanol/chloroform to 10% methanol/chloroform) gave an amber syrup. The syrup was dissolved in 10 mL of ethanol, combined with 0.25 mL of concentrated hydrochloric acid, and then concentrated under reduced pressure. The resulting syrup was crystallized from acetonitrile. The crystals were isolated by filtration, rinsed with cold acetonitrile, and dried with suction to give 181 mg of 1-[(1S)-1-[(4-hexoxyphenyl)methyl]-2-ethoxy-ethyl]imidazo[4,5-c]quinolin-4-amine as the hydrochloride salt (off-white powder). ¹H NMR (CD₃OD, 500 MHz) δ 8.62 (s, 1H), 8.35 (d, J=8.3 Hz, 1H), 7.76-7.68 (m, 2H), 7.57 (m, 1H), 7.02 (m, 2H), 6.66 (m, 2H), 5.65 (m, 1H), 4.04 (d, J=5.1, 1H), 3.80 (t, J=6.5 Hz, 1H), 3.55 (m, 2H), 3.43 (dd, J=5.8, 14.3 Hz, 1H), 3.32 (dd, J=9.1, 14.3 Hz, 1H), 1.66 (m, 2H), 1.41 (m, 2H), 1.36-1.29 (m, 4H), 1.13 (t, J=7.0 Hz, 3H), 0.92 (t, J=7.0 Hz, 3H).

Example 5

1-[(1 S)-1-(ethoxymethyl)-2-[4-(2-ethylhexoxy)phenyl]ethyl]imidazo[4,5-c]quinolin-4-amine

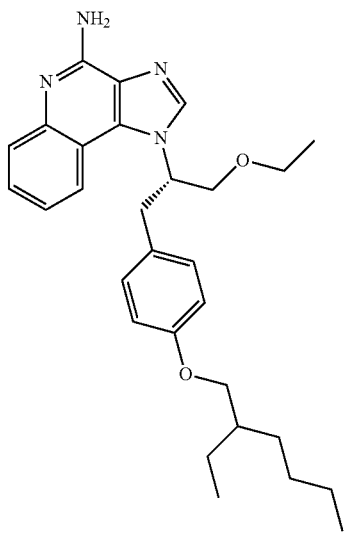 [SMILES: CCCCC(CC)COc1ccc(C[C@@H](COCC)n2cnc3c(N)nc4ccccc4c32)cc1]

33

Part A

To a stirred solution of 4-[(2S)-3-ethoxy-2-imidazo[4,5-c]quinolin-1-yl-propyl]phenol (500 mg, 1.44 mmol) in 4 mL of anhydrous DMF, Cs$_2$CO$_3$ (704 mg, 2.16 mmol) was added followed by the addition of 2-ethylhexyl iodide (258 microliters, 1.57 mmol). The reaction mixture was heated to 65° C. under an atmosphere of nitrogen. After stirring overnight, an additional 200 microliters of 2-ethylhexyl iodide and 600 mg of Cs$_2$CO$_3$ were added to the reaction mixture and heating was continued for 24 hours. The reaction mixture was then concentrated under reduced pressure. The resulting syrup was dissolved in 50 mL of ethyl acetate and washed successively with water (3×) and brine. The organic portion was dried over Na$_2$SO$_4$, filtered, and concentrated. Purification by column chromatography (SiO$_2$, 1% methanol/chloroform to 10% methanol/chloroform) gave 255 mg of 1-[(1S-1-(ethoxymethyl)-2-[4-(2-ethylhexoxy)phenyl]ethyl]imidazo[4,5-c]quinoline as an amber syrup.

Part B

A solution of 1-[(1S)-1-(ethoxymethyl)-2-[4-(2-ethylhexoxy)phenyl]ethyl]imidazo[4,5-c]quinoline (255 mg, 0.56 mmol) in 10 mL of dichloromethane was combined with 120 mg of MCPBA and stirred for 60 minutes. A 10% solution of Na$_2$CO$_3$ in water (10 mL) was then added and the mixture was diluted with an additional 10 mL of dichloromethane. The layers were separated. The organic portion was washed successively with water and brine, and then concentrated under reduced pressure. The resulting material was dissolved in 15 mL of dichloromethane followed by the addition of 6 mL of concentrated NH$_4$OH solution and para-toluenesulfonyl chloride (127 mg, 0.68 mmol). After stirring rapidly for 1 hour, the reaction mixture was diluted with 20 mL of dichloromethane and washed successively with water (3×) and brine. The organic portion was dried over Na$_2$SO$_4$, filtered, and concentrated under reduced pressure. Purification by column chromatography (SiO$_2$, 1% methanol/chloroform to 10% methanol/chloroform) followed by a second purification by column chromatography (SiO$_2$, 6% methanol/chloroform saturated with NH$_4$OH) gave an amber syrup. The syrup was dissolved in 10 mL of ethanol, combined with 0.25 mL of concentrated hydrochloric acid, and then concentrated under reduced pressure. The resulting syrup was crystallized from acetonitrile. The crystals were isolated by filtration, rinsed with cold acetonitrile, and dried under reduced pressure to give 72 mg of 1-[(1S)-1-(ethoxymethyl)-2-[4-(2-ethylhexoxy)phenyl]ethyl]imidazo[4,5-c]quinolin-4-amine as the hydrochloride salt (fluffy white solid). $^1$H NMR (CD$_3$OD, 500 MHz) δ 8.63 (s, 1H), 8.35 (d, J=8.3 Hz, 1H), 7.76-7.69 (m, 2H), 7.56 (m, 1H), 7.02 (m, 2H), 6.67 (m, 2H), 5.65 (m, 1H), 4.04 (d, J=5.1, 1H), 3.71 (d, J=5.6 Hz, 2H), 3.59-3.53 (m, 2H), 3.43 (dd, J=5.7, 14.3 Hz, 1H), 3.32 (dd, J=9.0, 14.3 Hz, 1H), 1.60 (m, 1H), 1.48-1.28 (m, 8H), 1.13 (t, J=7.0 Hz, 3H), 0.91 (t, J=7.0 Hz, 3H), 0.89 (t, J=7.5 Hz, 3H).

34

Example 6

1-[(1S)-1-[(4-benzyloxyphenyl)methyl]-2-ethoxy-ethyl]imidazo[4,5-c]quinolin-4-amine

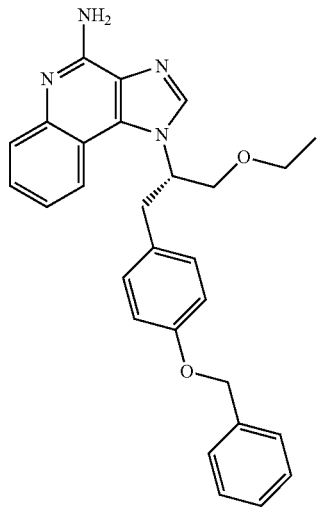 [SMILES: CCOC[C@H](Cc1ccc(OCc2ccccc2)cc1)n1cnc2c(N)nc3ccccc3c21]

Part A

To a stirred solution of 4-[(2S)-3-ethoxy-2-imidazo[4,5-c]quinolin-1-yl-propyl]phenol (498 mg, 1.43 mmol) in 4 mL of anhydrous DMF, Cs$_2$CO$_3$ (699 mg, 2.15 mmol) was added followed by the addition of benzyl bromide (187 microliters, 1.57 mmol). The reaction mixture was heated to 65° C. under an atmosphere of nitrogen. After stirring overnight, the reaction mixture was concentrated under reduced pressure. The resulting syrup was dissolved in 50 mL of ethyl acetate and washed successively with water (3×) and brine. The organic portion was dried over Na$_2$SO$_4$, filtered, and concentrated. Purification by column chromatography (SiO$_2$, 1% methanol/chloroform to 10% methanol/chloroform) gave 392 mg of 1-[(1S)-1-[(4-benzyloxyphenyl)methyl]-2-ethoxy-ethyl]imidazo[4,5-c]quinoline as a golden syrup.

Part B

A solution of 1-[(1S)-1-[(4-benzyloxyphenyl)methyl]-2-ethoxy-ethyl]imidazo[4,5-c]quinoline (392 mg, 0.90 mmol) in 25 mL of dichloromethane was combined with 193 mg of MCPBA and stirred for 50 minutes. A 10% solution of Na$_2$CO$_3$ in water (10 mL) was then added and the mixture was diluted with an additional 20 mL of dichloromethane. The layers were separated. The organic portion was washed successively with water and brine, and then concentrated under reduced pressure. The resulting material was dissolved in 15 mL of dichloromethane followed by the addition of 5 mL of concentrated NH$_4$OH solution and para-toluenesulfonyl chloride (188 mg, 0.99 mmol). After stirring rapidly for 1 hour, the reaction mixture was diluted with 20 mL of dichloromethane and washed successively with water (3×) and brine. The organic portion was dried over Na$_2$SO$_4$, filtered, and concentrated under reduced pressure. Purification by column chromatography (SiO$_2$, 1% methanol/chloroform to 10% methanol/chloroform) gave an amber syrup. The syrup was dissolved in 10 mL of ethanol, combined with 0.25 mL of concentrated hydrochloric acid, and then concentrated under reduced pressure. The resulting syrup was crystallized from acetonitrile. The crystals were isolated by filtration, rinsed with cold acetonitrile, and dried with suction to give 232 mg of 1-[(1S)-1-[(4-benzyloxyphenyl)methyl]-2-ethoxy-ethyl]imidazo[4,5-c]quinolin-4-amine as the hydrochloride salt (amber crystals). $^1$H NMR (CD$_3$OD, 500 MHz) δ 8.63 (s, 1H), 8.35 (d, J=8.3 Hz, 1H), 7.76-7.69 (m, 2H), 7.55 (m, 1H), 7.34-7.27 (m, 5H), 7.04 (m, 2H), 6.74 (m, 2H), 5.66 (m, 1H), 4.91 (s, 2H), 4.04 (d, J=5.1, 1H), 3.55 (m, 2H), 3.43 (dd, J=5.7, 14.2 Hz, 1H), 3.33 (dd, J=9.2, 14.3 Hz, 1H), 1.13 (t, J=7.0 Hz, 3H).

Cytokine Induction in Human Cells

Whole blood was obtained from healthy human donors and collected by venipuncture into vacutainer tubes or syringes containing EDTA. Human peripheral blood mononuclear cells (PBMC) were purified from the whole blood by density gradient centrifugation. Histopaque 1077 (15 mL, Sigma, St. Louis, Mo.) was transferred to 6×50 mL sterile polypropylene conical tubes. The Histopaque was overlayed with 15-25 mL of blood diluted 1:2 in Hank's Balanced Salts Solution (HBSS) (Gibco, Life Technology, Grand Island, N.Y.). The tubes were then centrifuged at 1370 rpm for 30 minutes at 20° C., with no brake (400λg, GH 3.8A Rotor).

The interface (buffy coat) containing the PBMC was collected and placed in a new sterile 50 mL conical polypropylene centrifuge tube. The PBMC were mixed with an equal volume of HBSS (about 20 mL from the interface and about 20 mL of HBSS), and then centrifuged at 1090 rpm, 10 minutes, 20° C., with brake (270λg, GH 3.8A Rotor). After completing centrifugation, the cells were resuspended in 2 to 3 mL ACK Red blood cell lysis buffer (ammonium chloride potassium solution, Gibco, Life Technology) and incubated for 2-5 minutes at 20° C. Next, HBSS (40 mL) was added to the cells, and the sample was centrifuged at 270×g for 10 minutes at 20° C. The supernatant was decanted, and the cell pellet was resuspended in 5 mL AIM V Medium (Gibco, Life Technology). Cell aggregates and debris were removed by filtering the cell solution through a BD Falcon 70 micron nylon cell strainer (BD Biosciences, San Jose, Calif.).

The number of viable cells was determined by counting with a Miltenyi FACS instrument (Miltenyi Biotec Inc., San Diego, Calif.) or by using a hemacytometer. For determining cell viability with a hemacytometer, the cells were diluted 1/10 in 0.4% trypan blue and HBSS (specifically, 50 microliter of trypan blue+40 microliter of HBSS+10 microliter of cell solution were added to a microfuge tube and mixed). Ten microliters of the diluted cells were then applied to the hemacytometer, and the number of viable PBMC were determined by microscopy.

The PBMC sample was then resuspended in 96-well plates at a concentration of 8×10$^5$ cells/well in 0.1 mL of AIM-V medium. Each compound was solubilized in DMSO to create a 3 mM stock solution. The stock solution was then further diluted with AIM-V medium to prepare the serial dilutions. The diluted compound (100 microliters) was then transferred to the PBMCs to achieve final compound concentrations of 30, 10, 3.3, 1.1, 0.37, 0.12, 0.04, 0.01 micromolar. The plates also had both positive and negative controls. The negative control wells contained only AIM-V medium with no example compound. The positive control wells contained imiquimod serially diluted to concentrations of 30, 10, 3.3, 1.1, 0.37, 0.12, 0.04, 0.01 micromolar. The plates were then cultured at 37° C./5% CO$_2$ for 21-24 hours. Cell-free supernatants were harvested by centrifuging the 96-well plates at 2100 rpm, 23° C. for 10 minutes. Approximately 160 microliter of the supernatant was then stored in a NUNC 96-well plate, covered with the compression cap and stored at −80° C. until the cytokine analysis was done.

IFN-alpha cytokine levels (picograms/mL) were measured by ELISA (human IFN-alpha, pan specific, Mabtech, Cincinnati, Ohio). IFN-gamma and TNF-alpha levels (picograms/mL) were measured by multiplex bead assay (magnetic beads, R & D Systems, Minneapolis, Minn.) according to the manufacturer's instructions.

The data was analyzed to determine the minimum effective concentration (MEC) for each compound at which induction of a particular cytokine was observed in the assay. Specifically, the minimum effective concentration of each compound (micromolar) was determined as the lowest concentration of the compound that induced a measured cytokine response at a level (picograms/mL) that was at least 2× greater than that observed with the negative control wells. The results are presented in Table 7. The designation "<0.01" indicates that cytokine induction was observed at the lowest concentration of compound evaluated in the assays.

TABLE 7

| Compound | MEC to Induce Cytokine (micromolar) | | |
| --- | --- | --- | --- |
| | IFN-alpha | IFN-gamma | TNF-alpha |
| Example 1 | 3.3 | 10 | 3.3 |
| Example 2 | 0.12 | 0.37 | 0.37 |
| Example 3 | ≤0.01 | ≤0.01 | ≤0.01 |
| Example 4 | ≤0.01 | ≤0.01 | ≤0.01 |
| Example 5 | 0.37 | 0.04 | ≤0.01 |
| Example 6 | ≤0.01 | ≤0.01 | ≤0.01 |

The complete disclosures of the patents, patent documents, and publications cited herein are incorporated by reference in their entirety as if each were individually incorporated. Various modifications and alterations to this invention will become apparent to those of ordinary skill in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of Formula (I), or salt thereof:

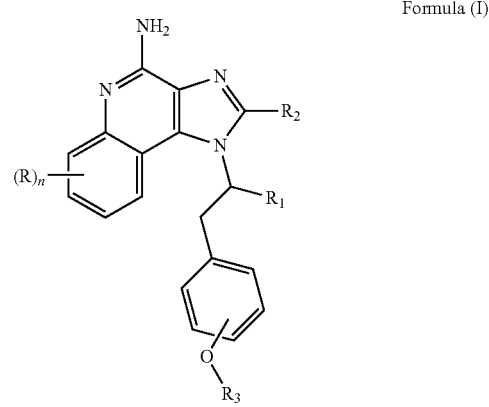

Formula (I)

wherein:

n is an integer of 0 or 1;

R is selected from the group consisting of halogen, hydroxy, alkyl, and alkoxy;

$R_1$ is —$C_{1-3}$alkylene-O—$C_{1-3}$alkyl;

$R_2$ is selected from the group consisting of hydrogen, methyl, ethyl, n-propyl, n-butyl, —$CH_2OCH_3$, —$CH_2OCH_2CH_3$, and —$CH_2CH_2OCH_3$; and $R_3$ is alkyl, aralkyl, wherein the alkyl or alkyl portion of the aralkyl can be optionally interrupted by one or more non-peroxidic —O— atoms, and wherein the aryl portion of the aralkyl can be optionally substituted with halogen, hydroxy, alkyl, alkoxy, or combinations thereof.

2. The compound or salt of claim 1, which is a compound of Formula (II), or salt thereof:

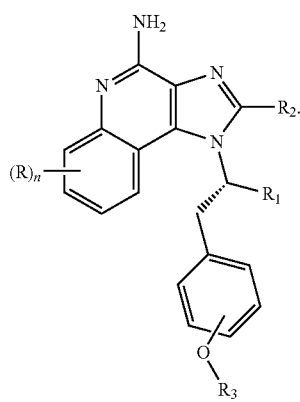

Formula (II)

3. The compound or salt of claim 1, which is a compound of Formula (III), or salt thereof:

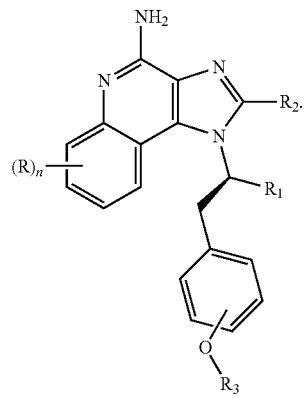

Formula (III)

4. The compound or salt of claim 3, wherein the O—$R_3$ group is in the para position.

5. The compound or salt of claim 1, wherein R is selected from the group consisting of halogen, hydroxy, —$C_{1-7}$alkyl, and —$C_{1-7}$alkoxy.

6. The compound or salt of claim 1, wherein n is 0.

7. The compound or salt of claim 1, wherein $R_1$ is —$CH_2OCH_3$ or —$CH_2OCH_2CH_3$.

8. The compound or salt of claim 1, wherein $R_2$ is selected from the group consisting of hydrogen, methyl, and ethyl.

9. The compound or salt of claim 1, wherein $R_3$ has at least 4 carbon atoms and up to 12 carbon atoms.

10. The compound or salt of claim 1, wherein $R_3$ is —$C_{4-12}$alkyl.

11. The compound or salt of claim 1, wherein $R_3$ is —$CH_2$-phenyl.

12. The compound or salt of claim 1 for use as a vaccine adjuvant.

13. A method of inducing biosynthesis of IFN-alpha in a human or animal comprising administering an effective amount of a compound or salt of claim 1 to the human or animal.

14. A method of inducing biosynthesis of TNF-alpha in a human or animal comprising administering an effective amount of a compound or salt of claim 1 to the human or animal.

15. A pharmaceutical composition comprising a therapeutically effective amount of a compound or salt of claim 1 in combination with a pharmaceutically acceptable carrier.

* * * * *